(12) United States Patent
He et al.

(10) Patent No.: US 7,022,873 B2
(45) Date of Patent: Apr. 4, 2006

(54) ANTIBIOTICS CYAN-416 A, CYAN-416 B, CYAN-416 C, CYAN-416 D AND CYAN-416 E, AND ESTER DERIVATIVES OF CYAN-416 B

(75) Inventors: Haiyin He, Washington Township, NJ (US); Ramunas Bigelis, Congers, NY (US)

(73) Assignee: Wyeth Holdings Corporation, Madison, NJ (US)

( * ) Notice: Subject to any disclaimer, the term of this patent is extended or adjusted under 35 U.S.C. 154(b) by 92 days.

(21) Appl. No.: 10/736,425

(22) Filed: Dec. 15, 2003

(65) Prior Publication Data

US 2004/0132812 A1    Jul. 8, 2004

Related U.S. Application Data

(60) Provisional application No. 60/434,004, filed on Dec. 17, 2002.

(51) Int. Cl.
C07C 69/74 (2006.01)
C07C 69/00 (2006.01)
C07C 49/84 (2006.01)
C07C 39/12 (2006.01)

(52) U.S. Cl. ............... 560/117; 560/138; 568/335; 568/718

(58) Field of Classification Search ............... 560/8, 560/51, 101, 102, 116, 117, 129, 130, 138, 560/140, 141; 568/303, 308, 325, 326, 329, 568/331, 335, 716, 717, 718, 719, 732, 733, 568/743, 763
See application file for complete search history.

(56) References Cited

FOREIGN PATENT DOCUMENTS

JP        06116281 A2    4/1994

OTHER PUBLICATIONS

Kornerup, A. and Wanscher, J.H., Methuen Handbook of Colour, 3rd Ed., 1978, pp. 252, Eyre Methuen, London.
Law, Kai-Kwong, et al.., Synthesis of Pinselic Acid and Pinselin, J. Org. Chem., 1979, pp. 4452-4453, vol. 44(24).
"Nosocomial Enterococci Resistant to Vancomycin", Morbidity and Mortality Weekly Report, 1993, pp. 597-598, vol. 42(30).
Handwergers, et al., Clin. Infect. Dis., 1993(16), pp. 750-755.
Tabata, et al., "New Anticoccidial Agents Produced by Humicola sp.: Production, Isolation and Physico-Chemical and Biological Properties", J. Antibiot., 1993, pp. 749-755, vol. 46(5).
Tabata, Noriko, et al., "Structure and Biosynthesis of Xanthoquinodins, Anticoccidial Antibiotics", J. Am. Chem. Soc., 1993, pp. 8558-8564, vol. 115(19).
Tabata, Noriko, et al., Xanthoquinodin B3, a New Anticoccidial Agent Produced by Humicola sp., FO-888, J. Antibiot., 1996, pp. 267-271, vol. 49(3).
JP 06116281 A2, Satoshi Omura, et al., Apr. 26, 1994, English Translation.

*Primary Examiner*—Johann Richter
*Assistant Examiner*—Karl Puttlitz
(74) *Attorney, Agent, or Firm*—Daniel B. Moran

(57) ABSTRACT

The invention relates to new antibiotics designated Cyan-416A, Cyan 416B, Cyan-416C, Cyan-416D and Cyan-416E to their production by fermentation of *Acremonium* sp. NRRL 30631 to methods for recovery and concentration from the crude solutions, and to a process for purification and to semisynthetic ethers of Cyan-416B.

13 Claims, 15 Drawing Sheets

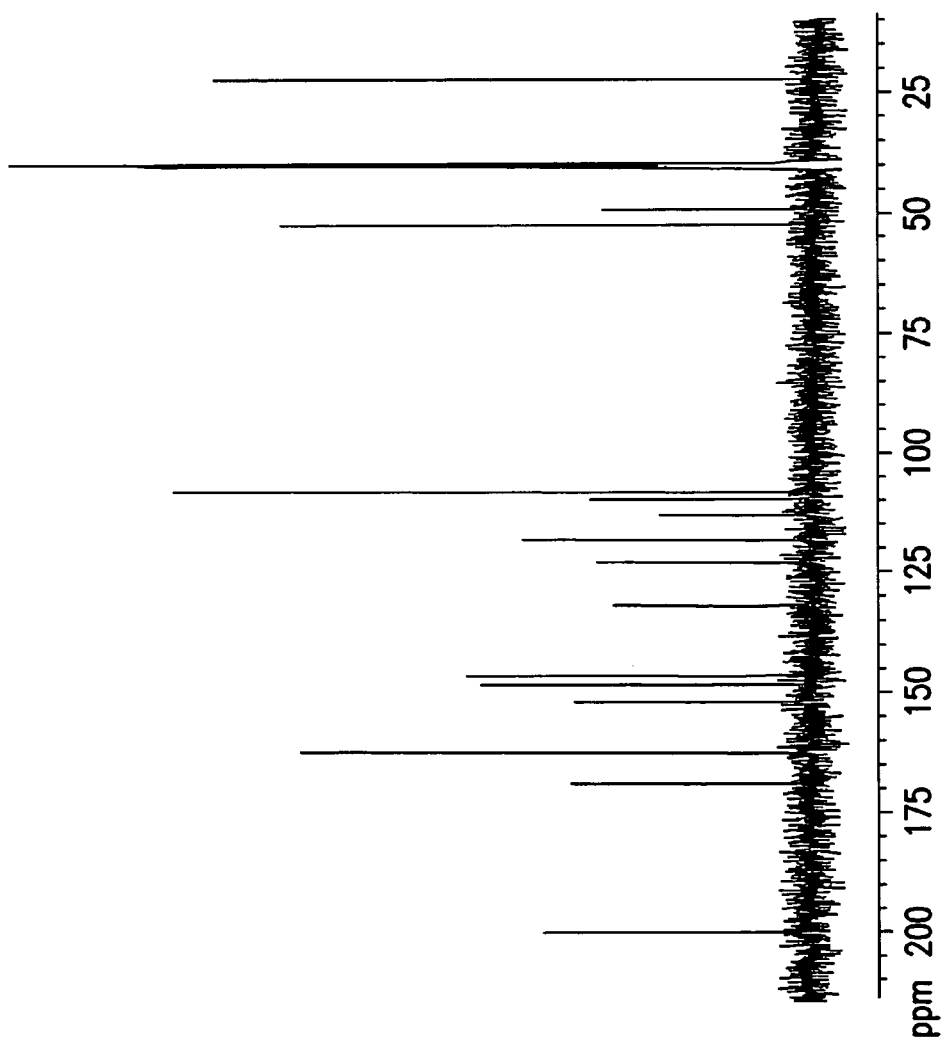

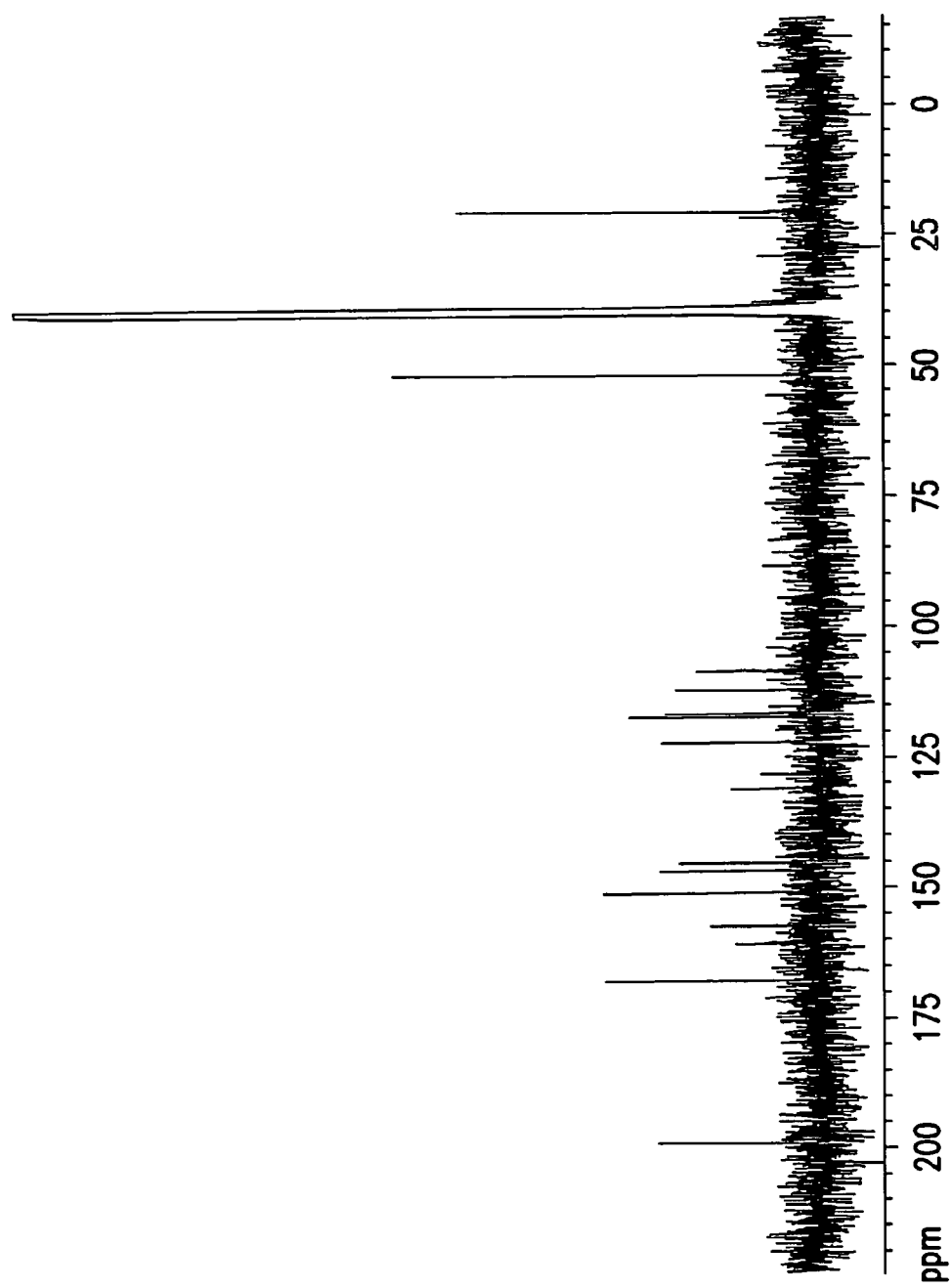

ANTIBIOTICS CYAN-416 A, CYAN-416 B, CYAN-416 C, CYAN-416 D AND CYAN-416 E, AND ESTER DERIVATIVES OF CYAN-416 B

"This application claims priority from copending provisional application, application No. 60/434,004 filed Dec. 17, 2002 the entire disclosure of which is hereby incorporated by reference"

FIELD OF THE INVENTION

The invention relates to new antibiotics designated Cyan-416 A, Cyan-416 B, Cyan-416 C, Cyan-416 D, and Cyan-416 E, to production by fermentation, to methods for recovery and concentration from the crude solutions, to process for purification of Cyan-416 A, Cyan-416 B, Cyan-416 C, Cyan-416 D and Cyan-416 E and to the synthesis of the esters of Cyan-416 B.

BACKGROUND OF THE INVENTION

New improved antibiotics are continually in demand, for the treatment of diseases in man. Antibiotic resistant organisms are continually a problem, with Vancomycin the last defense, particularly in hospitals. Especially in hospitals, isolates, which are vancomycin resistant, are becoming more common. A recent survey found 7.9% of Enterococci in United States hospitals are now vancomycin resistant. "Nosocomial Enterococci Resistant to Vancomycin" Morbidity and Mortality Weekly Report 42(30):597–598(1993). Further resistance of Vancomycin and other antibiotics to Enterococcus faecium is reported, Handwergers. et al., Clin. Infect. Dis. 1993(16),750–755. Resistance organisms are also a problem for other important antibiotics, which includes methicillin.

Clearly, antibiotic resistance is a growing public health problem and having new antibiotics available could provide additional options for physicians in treatment regimens.

The medical community recognizes that there is an ongoing need for additional antibiotics. The search for new antibiotics which exhibit antibacterial activity against vancomycin-resistant isolates and having structures which are not derivatives of vancomycin are particularly appealing.

Antibiotics described in the literature include: Xanthoquinodins, Tabata, Noriko; Suzumura, Yasuko; Tomoda, Hiroshi; Masuma, Rokuro; Haneda, Katsuji; Kishi, Masanori; Iwai, Yuzuru; Omura, Satoshi. Xanthoquinodins, new anticoccidial agents produced by *Humicola* sp.: production, isolation, and physico-chemical and biological properties. *J. Antibiot* (1993),46(5),749–55. Tabata, Noriko; Tomoda, Hiroshi; Matsuzaki, Keiichi; Omura, Satoshi. Structure and biosynthesis of xanthoquinodins, anticoccidial antibiotics. *J. Am. Chem. Soc.* (1993), 115(19), 8558–64. Omura, Satoshi; Koda, Hiroshi; Masuma, Rokuro; Haneda, Katsuji; Iwai, Yuzuru. Anticoccidial agents manufactured with *Humicola*. (1994), 25 pp., JP 06116281 A2 19940426. Tabata, Noriko; Tomoda, Hiroshi; Iwai, Yuzuru; Omura, Satoshi. Xanthoquinodin B3, a new anticoccidial agent produced by *Humicola* sp. FO-888. *J. Antibiot.* (1996), 49(3), 267–71 and Pinselic acid, related to Cyan-416 D is reported by Law, Kai-Kwong; Chan, Tze-Lock; Tam, Shang Wai; Shatin, N. T. Synthesis of pinselic acid and pinselin. *J. Org. Chem.* (1979), 44(24), 4452–3.

However, all of the above-disclosed antibiotics are distinct from the present invention.

BRIEF SUMMARY OF THE INVENTION

The present invention relates to the following antibiotic compounds:

Antibiotic Cyan-416 A having the structure:

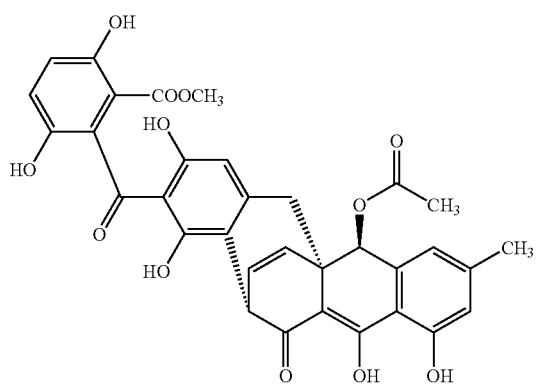

Antibiotic Cyan-416 B having the structure:

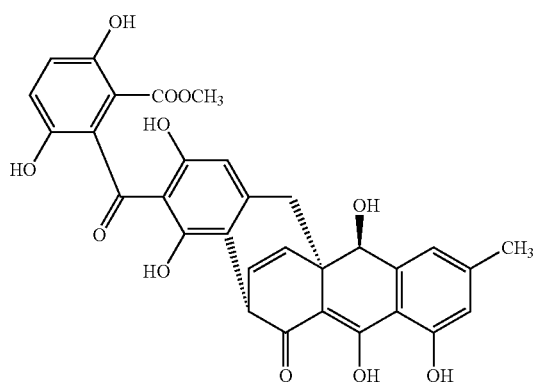

Antibiotic Cyan-416 C having the structure:

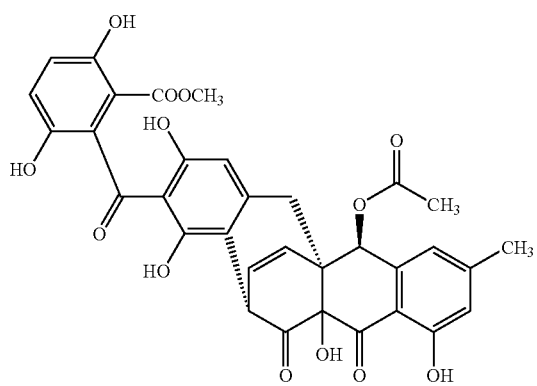

Antibiotic Cyan-416 D having the structure:

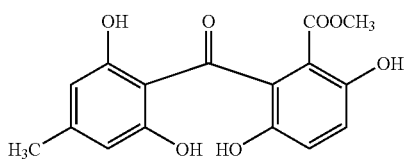

Antibiotic Cyan-416 E having the structure:

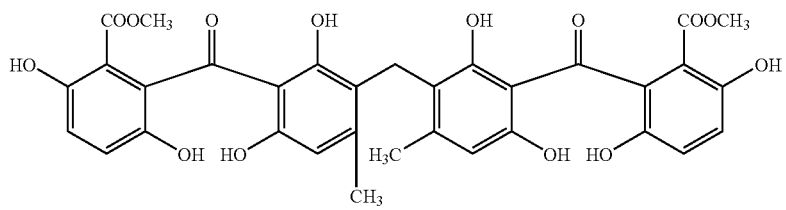

and further relates to esters of Cyan-416 B of Formula I and a process for the preparation thereof Formula I

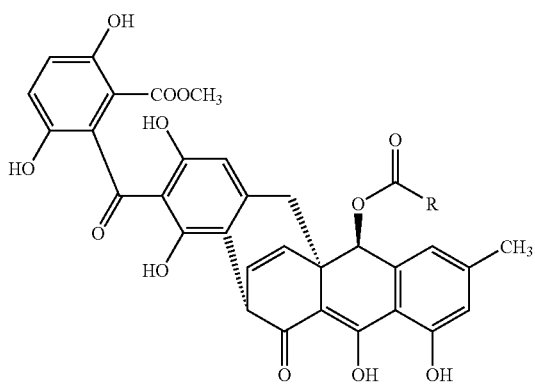

where R is straight or branched alkyl of 1 to 10 carbon atoms, alkenyl of 2 to 10 carbon atoms, cycloalkyl of 3 to 10 carbon atoms and cycloalkenyl of 3 to 10 carbon atoms.

The present invention includes within its scope the agents in dilute form, as a crude concentrate, and in pure form. The present invention also relates to the use of the compounds according to the invention in antimicrobial compositions and as an antiseptic, or disinfectant.

It is an object of this invention to provide compounds of the invention, which are shown to possess antibacterial activity, especially against vancomycin resistant bacterial isolates and in particular having a chemical structure unlike vancomycin.

BRIEF DESCRIPTION OF THE DRAWINGS

FIG. 14. shows carbon-13 nuclear magnetic resonance spectrum of Cyan-416 D in DMSO-$d_6$ at 100 MHz.

FIG. 15. shows carbon-13 nuclear magnetic resonance spectrum of Cyan-416 E in DMSO-$d_6$ at 100 MHz.

DESCRIPTION OF THE PREFERRED EMBODIMENTS

The invention relates to new antibiotics Cyan-416 A, Cyan-416 B, Cyan-416 C, Cyan-416 D and Cyan-416 E, to the production of the antibiotics by fermentation, to methods for the recovery and concentration of the antibiotics from crude solutions, and to processes for the purification of the antibiotics. The invention includes within its scope the new antibiotics in diluted form, as crude concentrate and in pure form. The novel antibiotics are useful as antibacterial agents.

As used herein the term alkyl means a branched or straight chain radical having from 1 to 10 carbon atoms.

As used herein the term alkenyl as used herein means an unsaturated branched or straight chain radical having from 2 to 10 carbon atoms. Alkenyl, may be used synonymously with the term olefin and includes alkylidenes. Exemplary alkenyl groups include but are not limited to ethylene, propylene, and isobutylene.

As used herein the term cycloalkyl means a saturated monocyclic ring having from 3 to 10 carbon atoms. Exemplary cycloalkyl rings include but are not limited to cyclopropyl, cyclobutyl, cyclopentyl, and cyclohexyl, As used herein the term cycloalkenyl means a non-aromatic monocyclic ring system containing a carbon-carbon double bond and having about 3 to about 10 atoms. Preferred monocyclic cycloalkenyl rings include cyclopentenyl and cyclohexenyl.

The new antibiotics designated Cyan-416 A, Cyan-416 B, Cyan-416 C, Cyan-416 D and Cyan-416 E are formed during the fermentation of *Acremonium* sp. NRRL 30631.

The structure of the new antibiotic Cyan-416 A is:

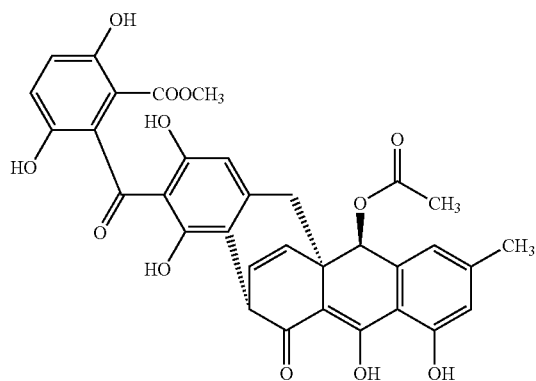

Figure 1:
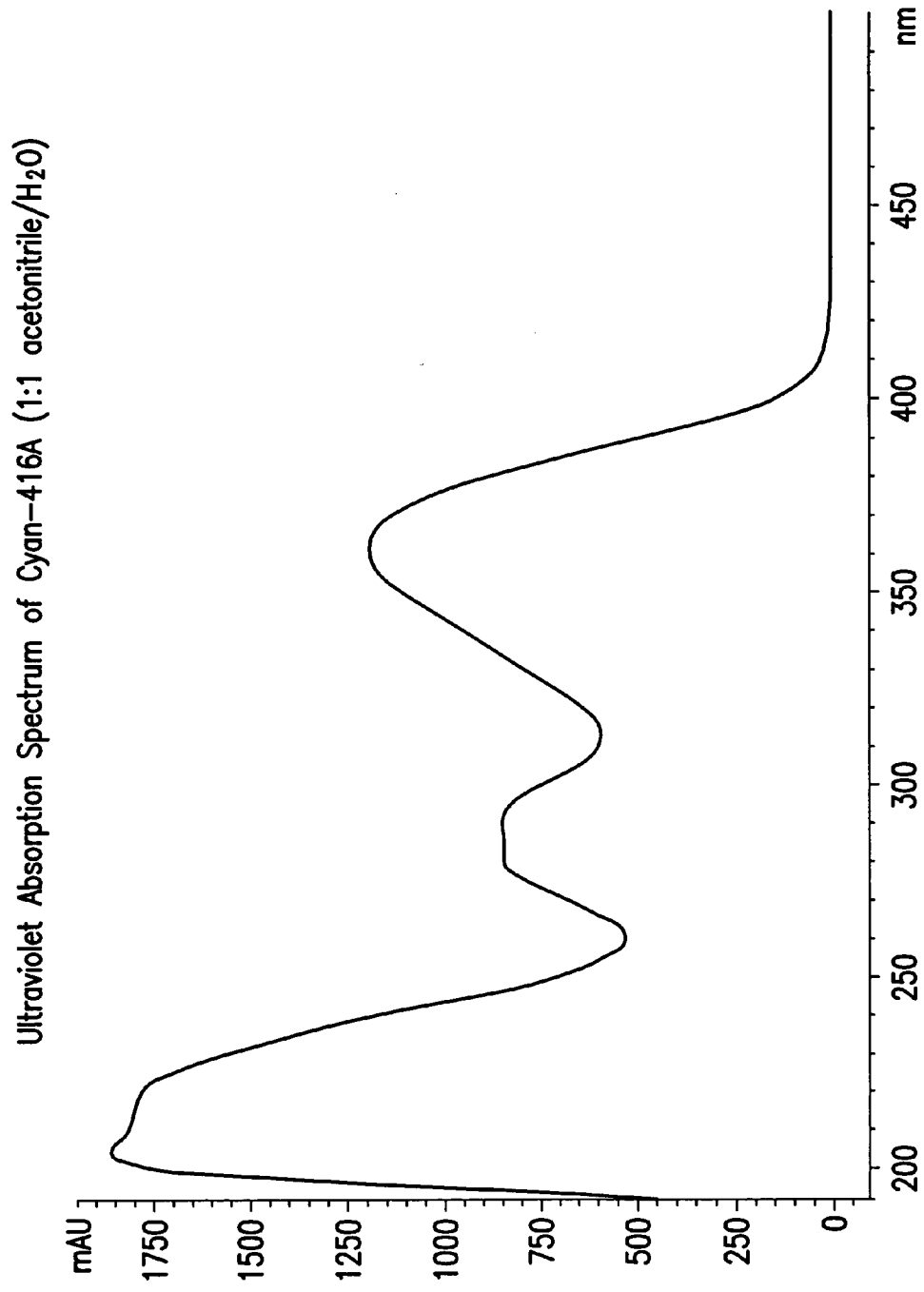
FIG. 1. shows ultraviolet absorption spectrum of Cyan-416 A.
Figure 6:
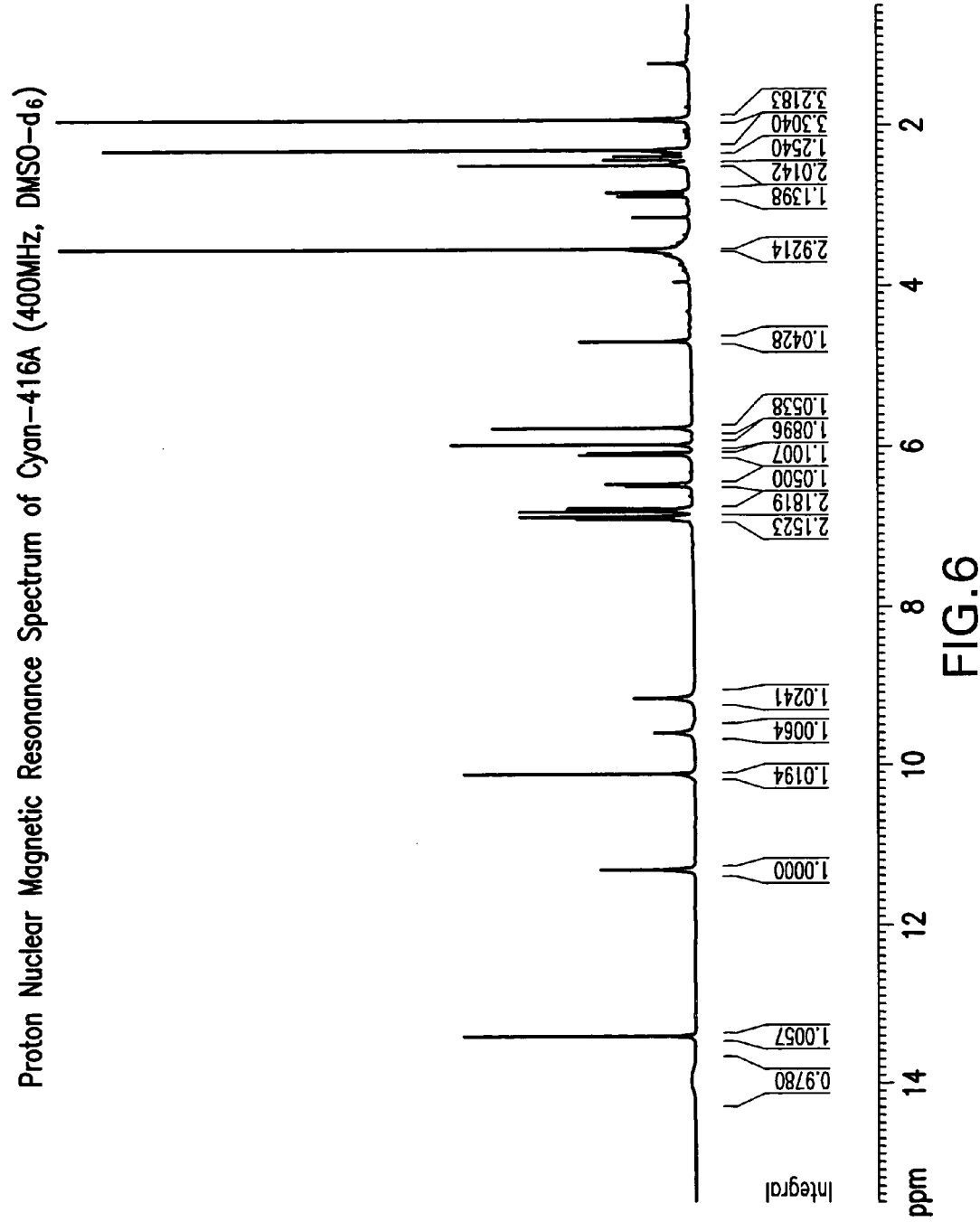
FIG. 6. shows proton nuclear magnetic resonance spectrum of Cyan-416 A in DMSO-$d_6$ at 400 MHz.
Figure 11:
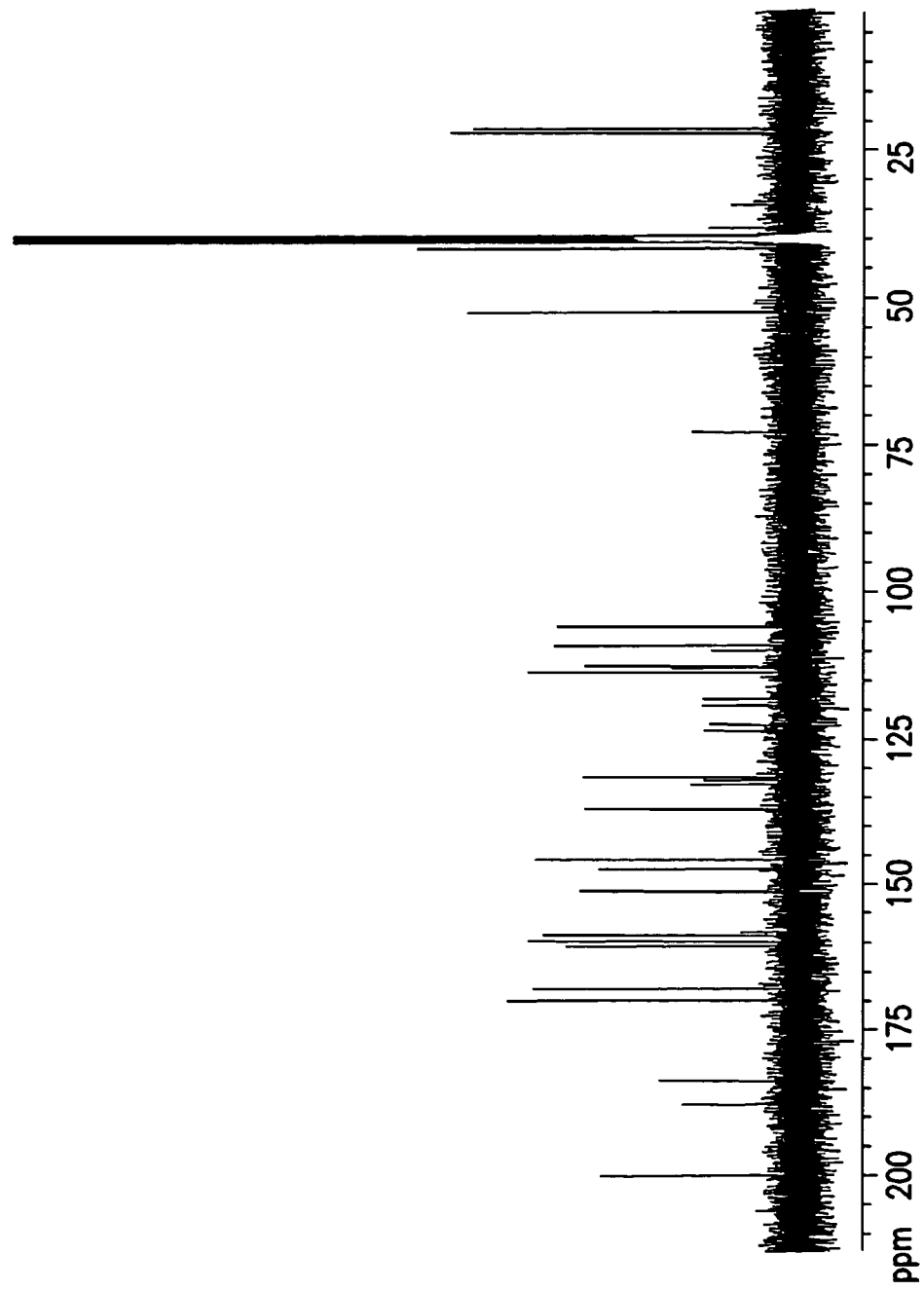
FIG. 11. shows carbon-13 nuclear magnetic resonance spectrum of Cyan-416 A in DMSO-$d_6$ at 100 MHz.

The physico-chemical characteristics of Cyan-416 A are as follows:
1. Molecular weight: 614 (ESIMS);
2. Apparent molecular formula: $C_{33} H_{26} O_{12}$;
3. High-resolution Fourier transform ion cyclotron resonance mass spectrum (positive): m/z 615.14913 (MH$^+$, $C_{33} H_{27} O_{12}$ requires 615.14970);
4. Ultraviolet absorption spectrum as shown in FIG. 1;
5. Proton nuclear magnetic resonance signals as shown in FIG. 6 (400 MHz, DMSO-d$_6$);
6. Carbon-13 nuclear magnetic resonance signals as shown in FIG. 11 (100 MHz, DMSO-d$_6$), with significant signals listed below:

| | | | | | |
|---|---|---|---|---|---|
| 199.88 | 187.56 | 183.39 | 169.69 | 167.70 | 160.45 |
| 159.55 | 158.48 | 151.00 | 147.22 | 145.61 | 145.50 |
| 136.70 | 132.37 | 131.68 | 131.09 | 123.18 | 122.04 |
| 118.88 | 117.66 | 113.08 | 112.44 | 112.06 | 109.48 |
| 108.69 | 105.45 | 72.46 | 52.01 | 41.08 | 37.62 |
| 33.93 | 21.52 | 20.78 | | | |

The structure of the new antibiotic Cyan-416 B is:

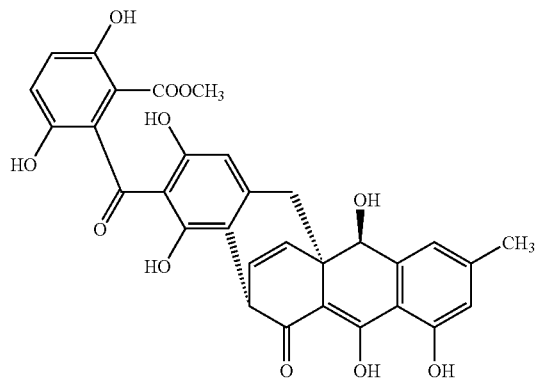

Figure 2:
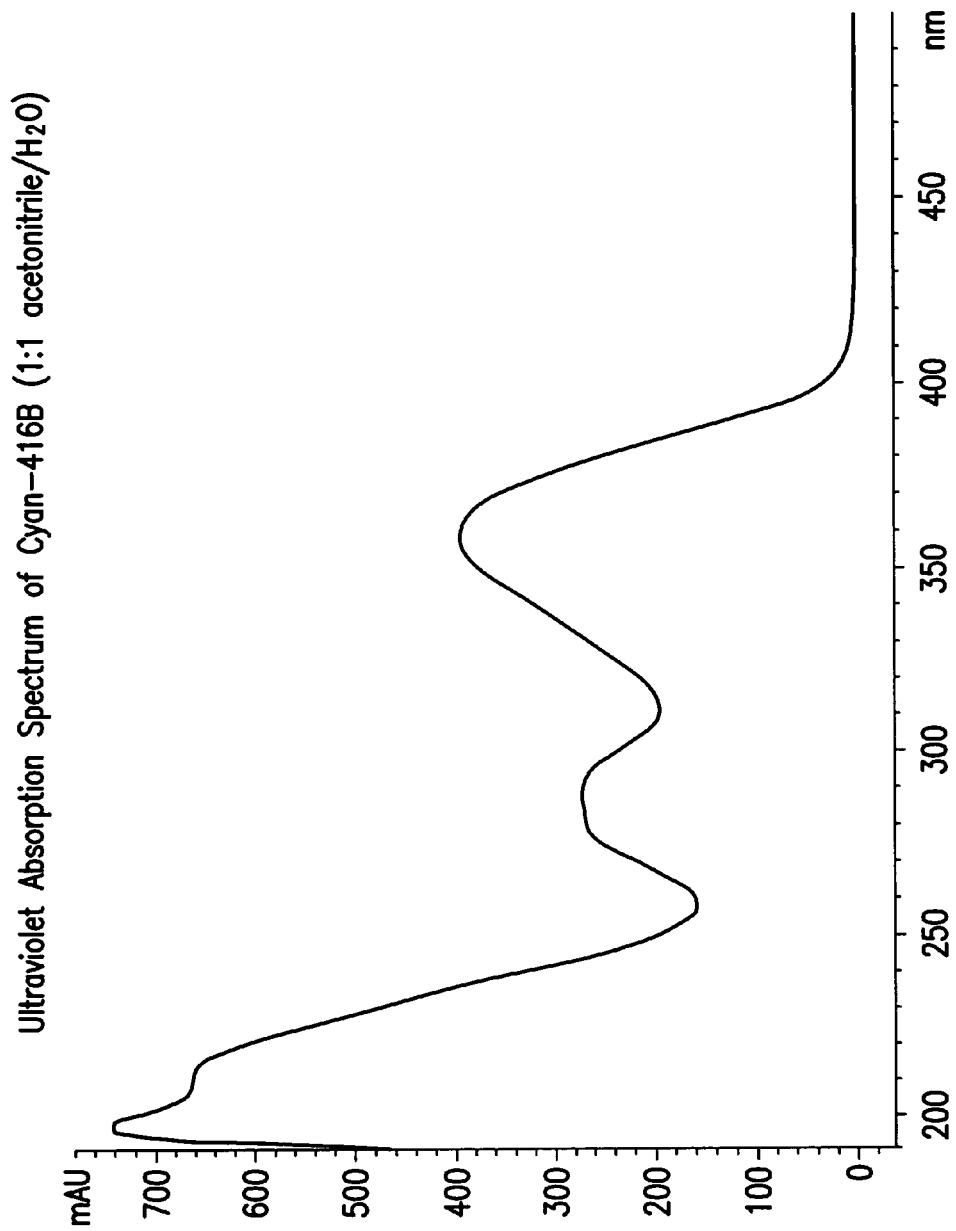
FIG. 2. shows ultraviolet absorption spectrum of Cyan-416 B.
Figure 7:
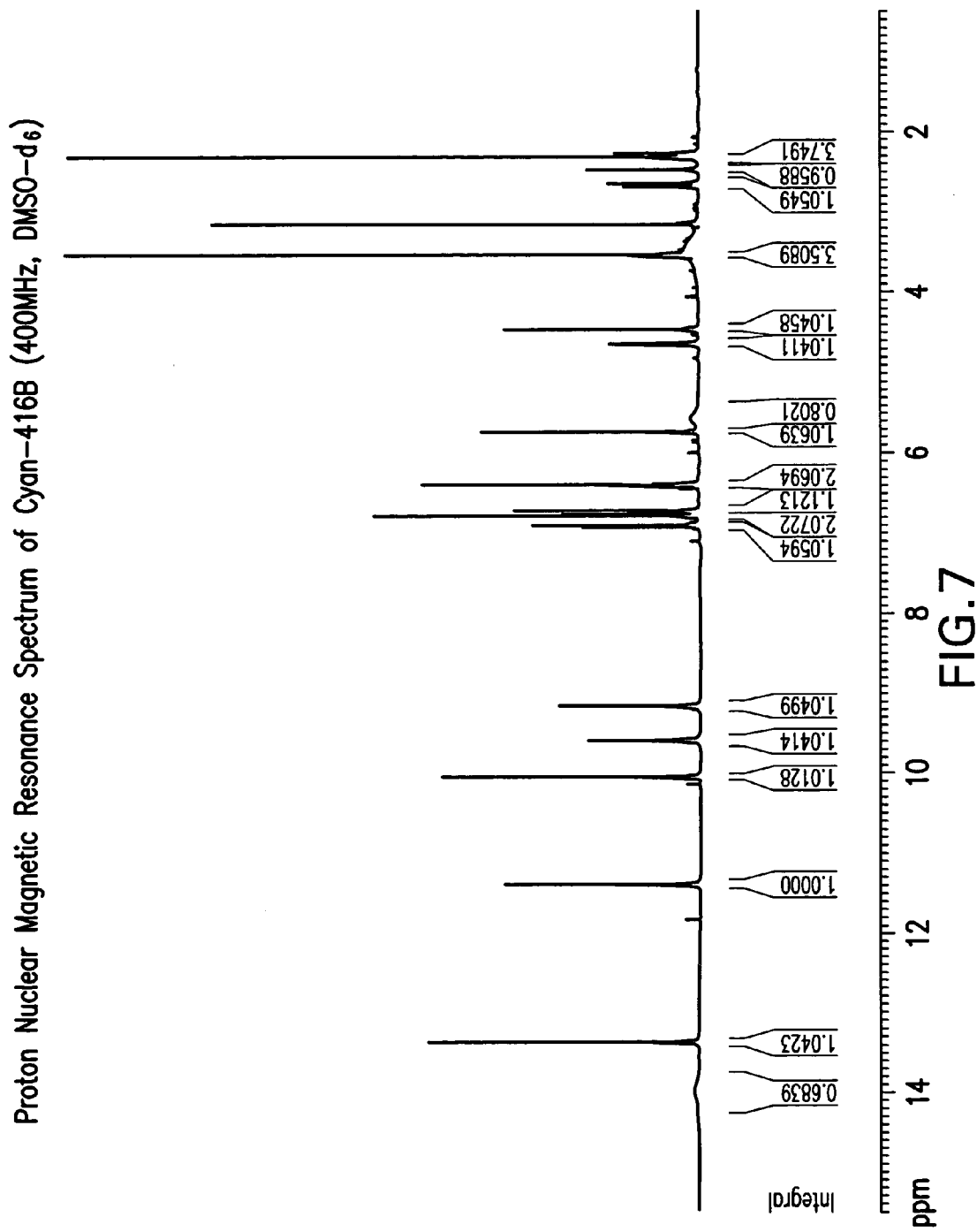
FIG. 7. shows proton nuclear magnetic resonance spectrum of Cyan-416 B in DMSO-$d_6$ at 400 MHz.
Figure 12:
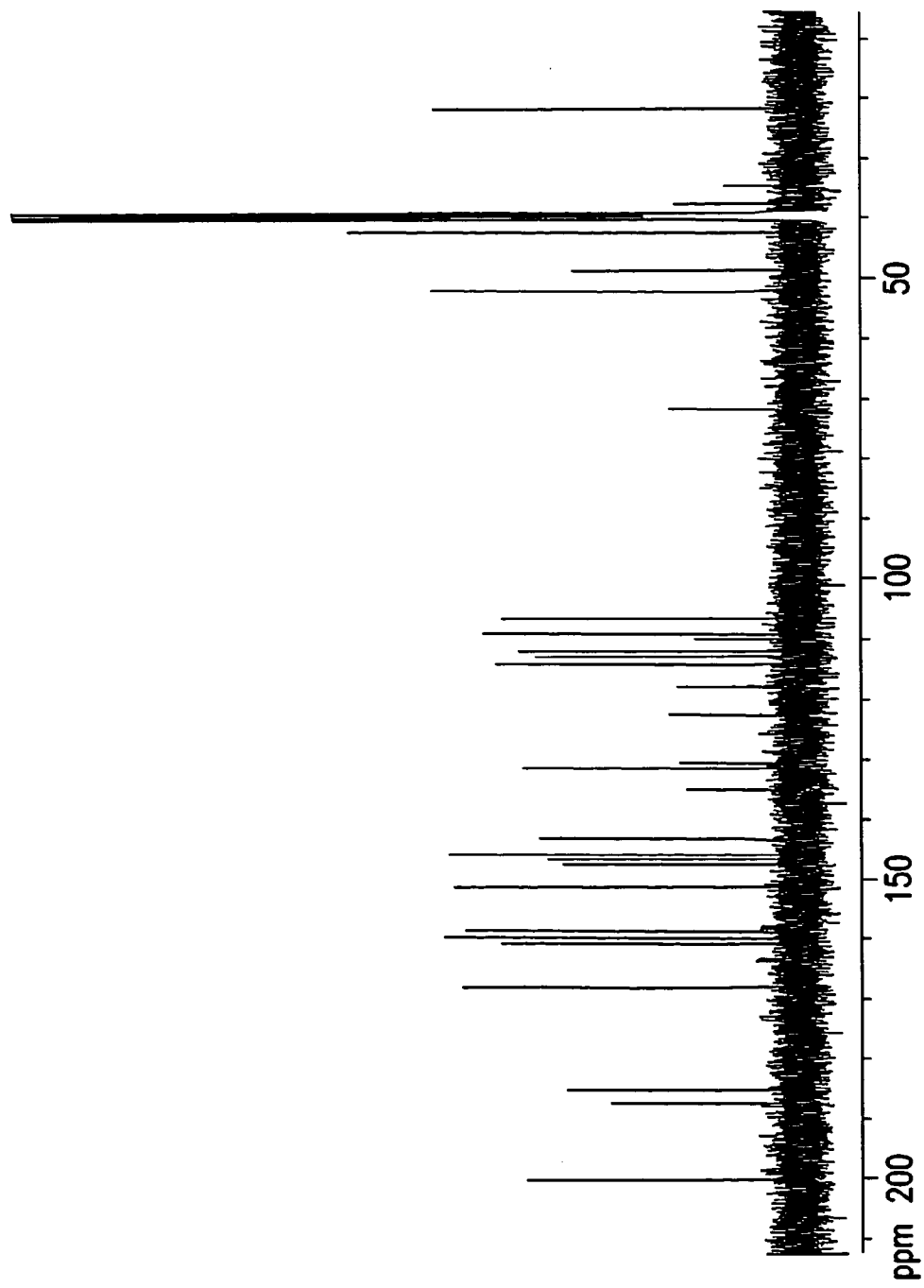
FIG. 12. shows carbon-13 nuclear magnetic resonance spectrum of Cyan-416 B in DMSO-$d_6$ at 100 MHz.

The physico-chemical characteristics of Cyan-416 B are as follows:
1. Molecular weight: 572 (ESIMS);
2. Apparent molecular formula: $C_{31} H_{24} O_{11}$;
3. High-resolution Fourier transform ion cyclotron resonance mass spectrum (positive): m/z 573.13900 (MH$^+$, $C_{31} H_{25} O_{11}$ requires 573.13968);
4. Ultraviolet absorption spectrum as shown in FIG. 2;
5. Proton nuclear magnetic resonance signals as shown in FIG. 7 (400 MHz, DMSO-d$_6$);
6. Carbon-13 nuclear magnetic resonance signals as shown in FIG. 12 (100 MHz, DMSO-d$_6$), with significant signals listed below:

| | | | | | |
|---|---|---|---|---|---|
| 199.86 | 187.03 | 184.84 | 167.76 | 160.51 | 159.50 |
| 158.39 | 151.04 | 147.07 | 146.31 | 145.53 | 142.73 |
| 134.69 | 131.16 | 130.18 | 122.22 | 122.08 | 117.64 |
| 117.36 | 113.77 | 112.45 | 111.63 | 109.45 | 108.64 |
| 106.16 | 71.39 | 52.02 | 42.37 | 37.41 | 34.44 |
| 21.56 | | | | | |

The structure of the new antibiotic Cyan-416 C is:

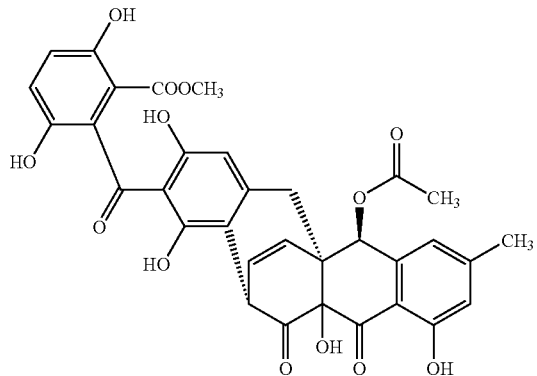

Figure 3:
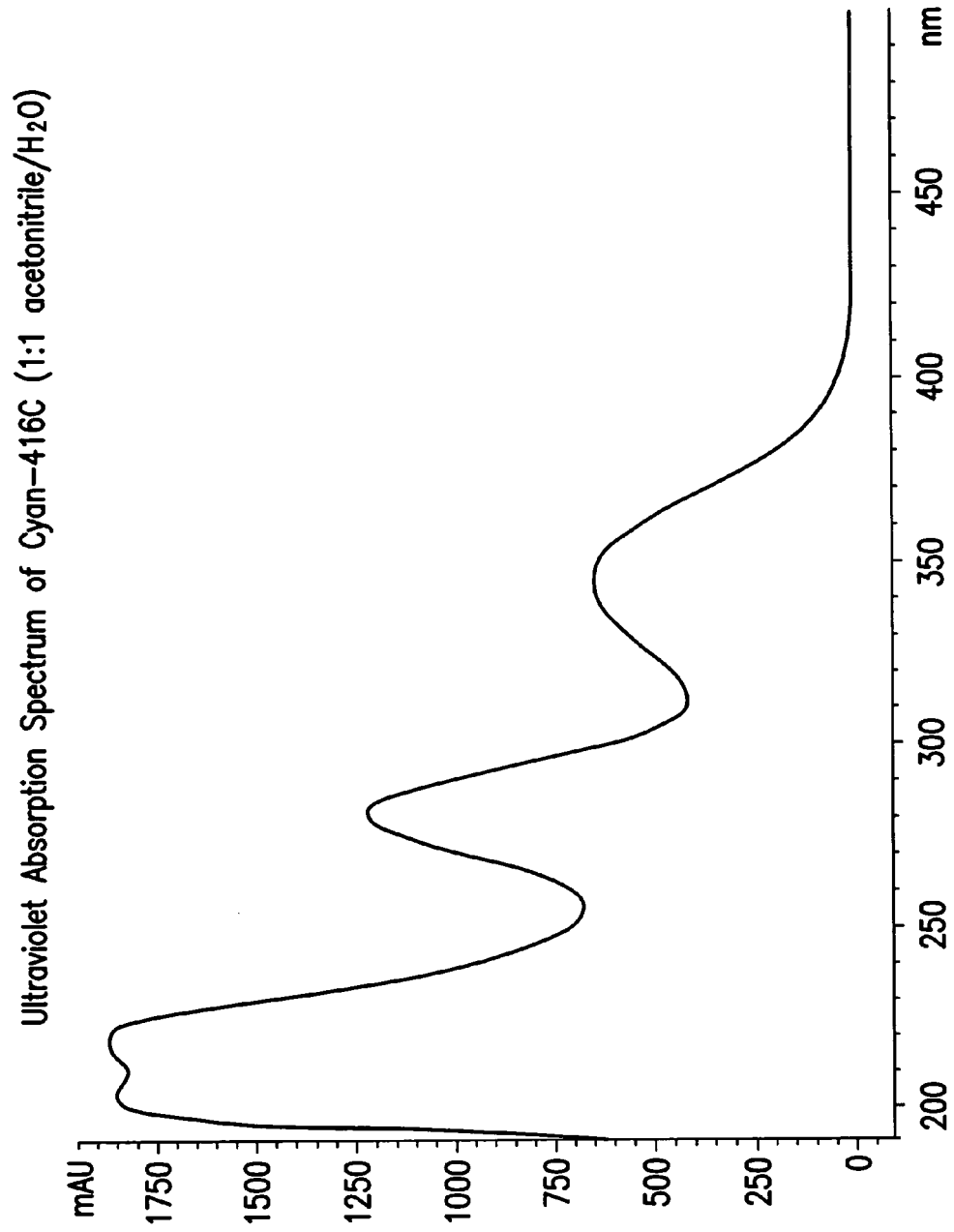
FIG. 3. shows ultraviolet absorption spectrum of Cyan-416 C.
Figure 8:
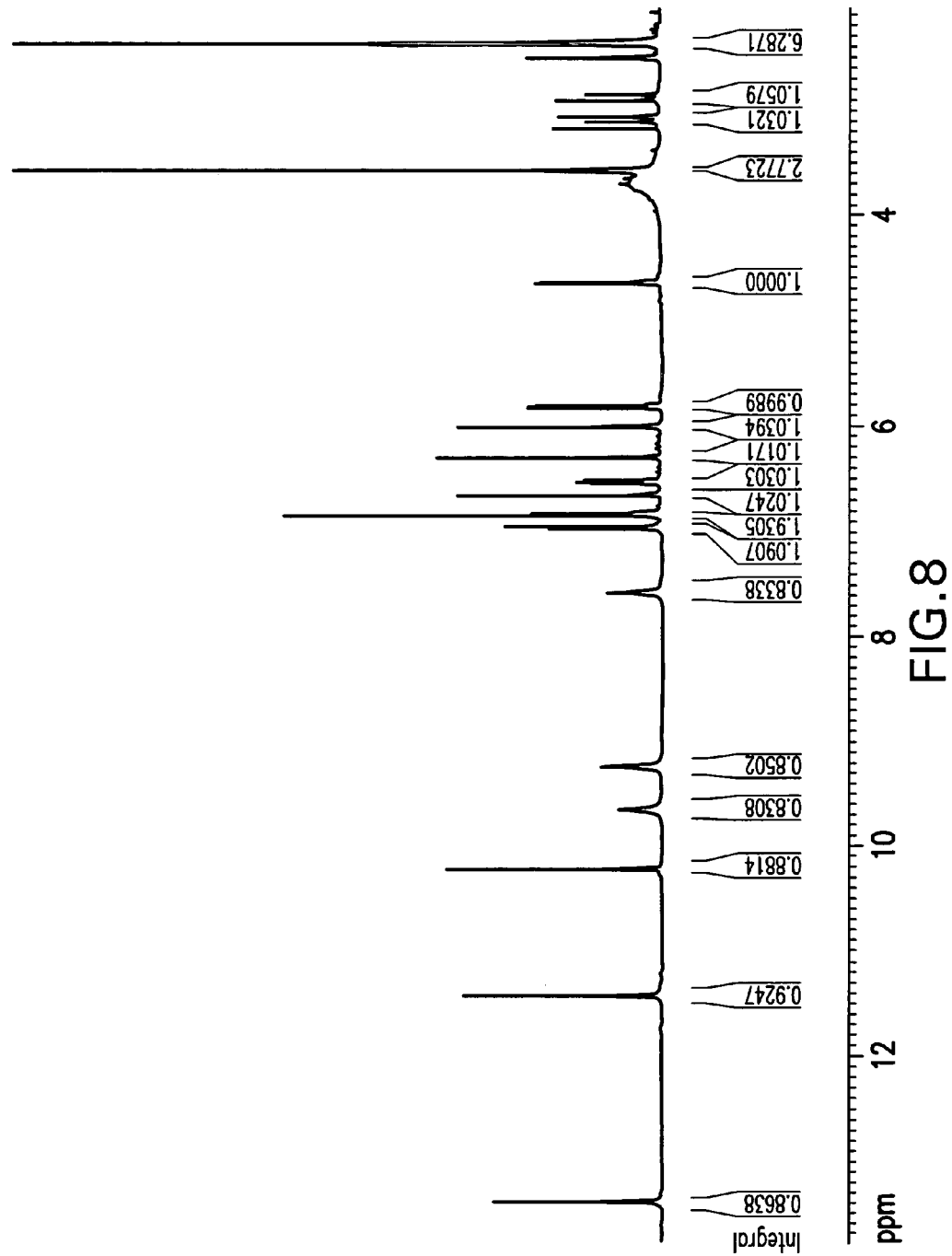
FIG. 8. shows proton nuclear magnetic resonance spectrum of Cyan-416 C in DMSO-$d_6$ at 400 MHz.
Figure 13:
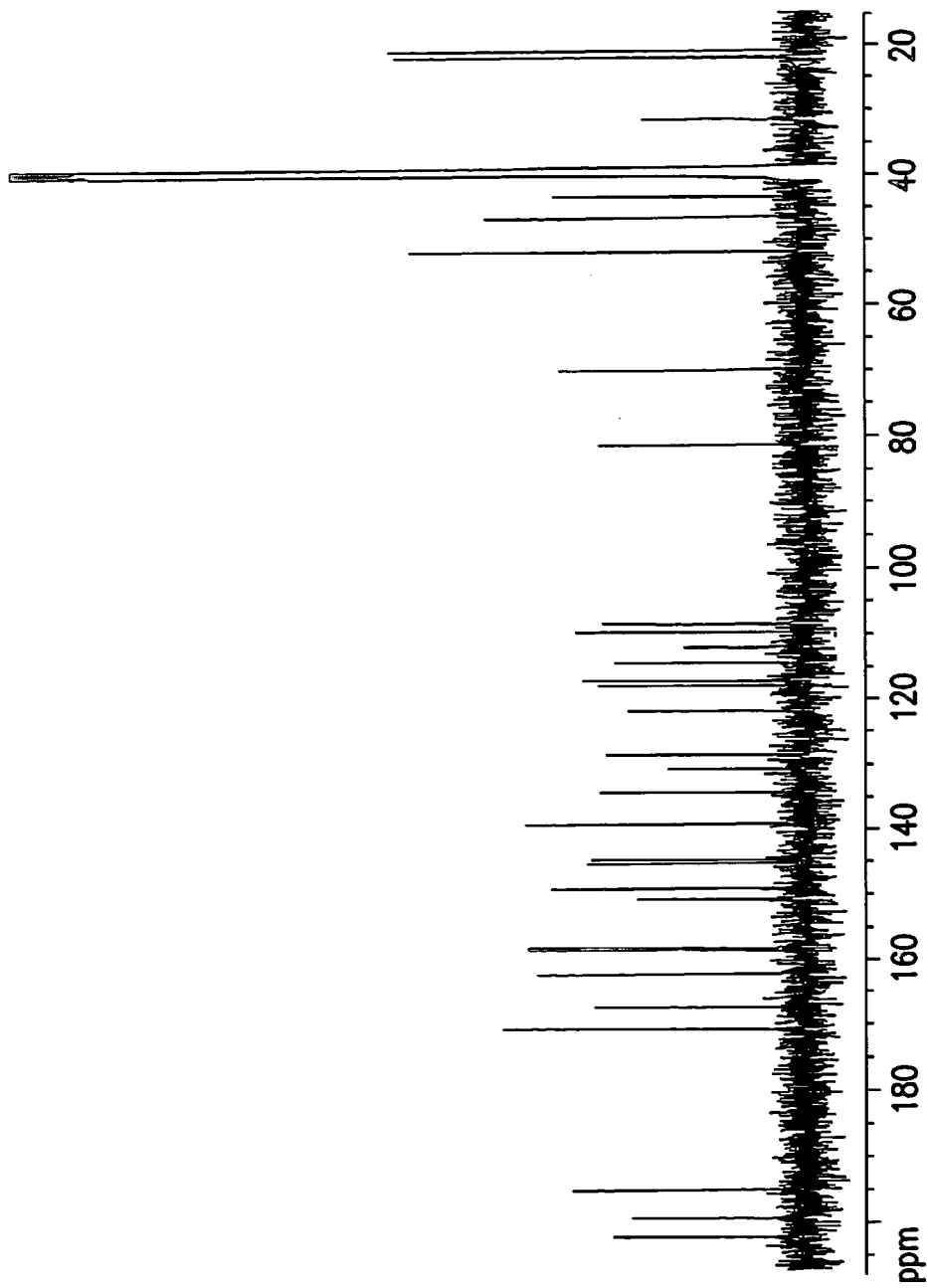
FIG. 13. shows carbon-13 nuclear magnetic resonance spectrum of Cyan-416 C in DMSO-$d_6$ at 100 MHz.

The physico-chemical characteristics of Cyan-416 C are as follows:
1. Molecular weight: 630 (ESIMS);
2. Apparent molecular formula: $C_{33}H_{26}O_{13}$;
3. High-resolution Fourier transform ion cyclotron resonance mass spectrum (positive): m/z 631.14490 (MH$^+$, $C_{33}H_{27}O_{13}$ requires 631.14462);
4. Ultraviolet absorption spectrum as shown in FIG. 3;
5. Proton nuclear magnetic resonance signals as shown in FIG. 8 (400 MHz, DMSO-d$_6$);
6. Carbon-13 nuclear magnetic resonance signals as shown in FIG. 13 (100 MHz, DMSO-d$_6$), with significant signals listed below:

| | | | | | |
|---|---|---|---|---|---|
| 202.78 | 199.83 | 195.54 | 171.03 | 167.72 | 162.68 |
| 158.96 | 158.55 | 151.09 | 149.44 | 145.55 | 145.00 |
| 139.53 | 134.60 | 131.00 | 128.72 | 122.14 | 118.24 |
| 117.69 | 117.38 | 114.67 | 112.33 | 109.90 | 108.85 |
| 108.60 | 81.51 | 70.12 | 51.95 | 46.74 | 43.40 |
| 31.51 | 21.84 | 20.86 | | | |

The structure of the new antibiotic Cyan-416 D is:

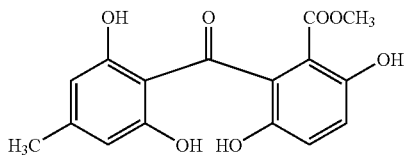

Figure 4:
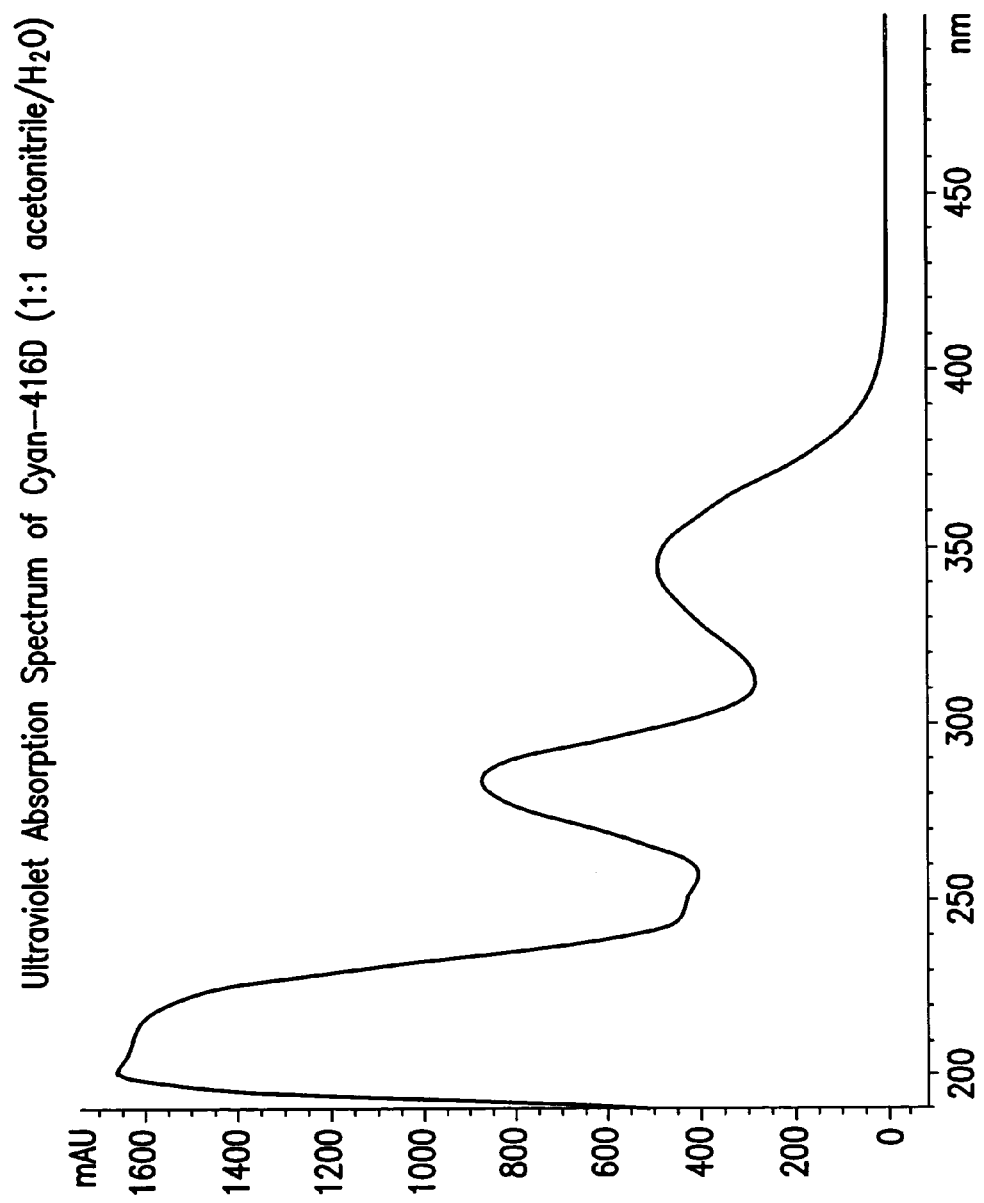
FIG. 4. shows ultraviolet absorption spectrum of Cyan-416 D.
Figure 9:
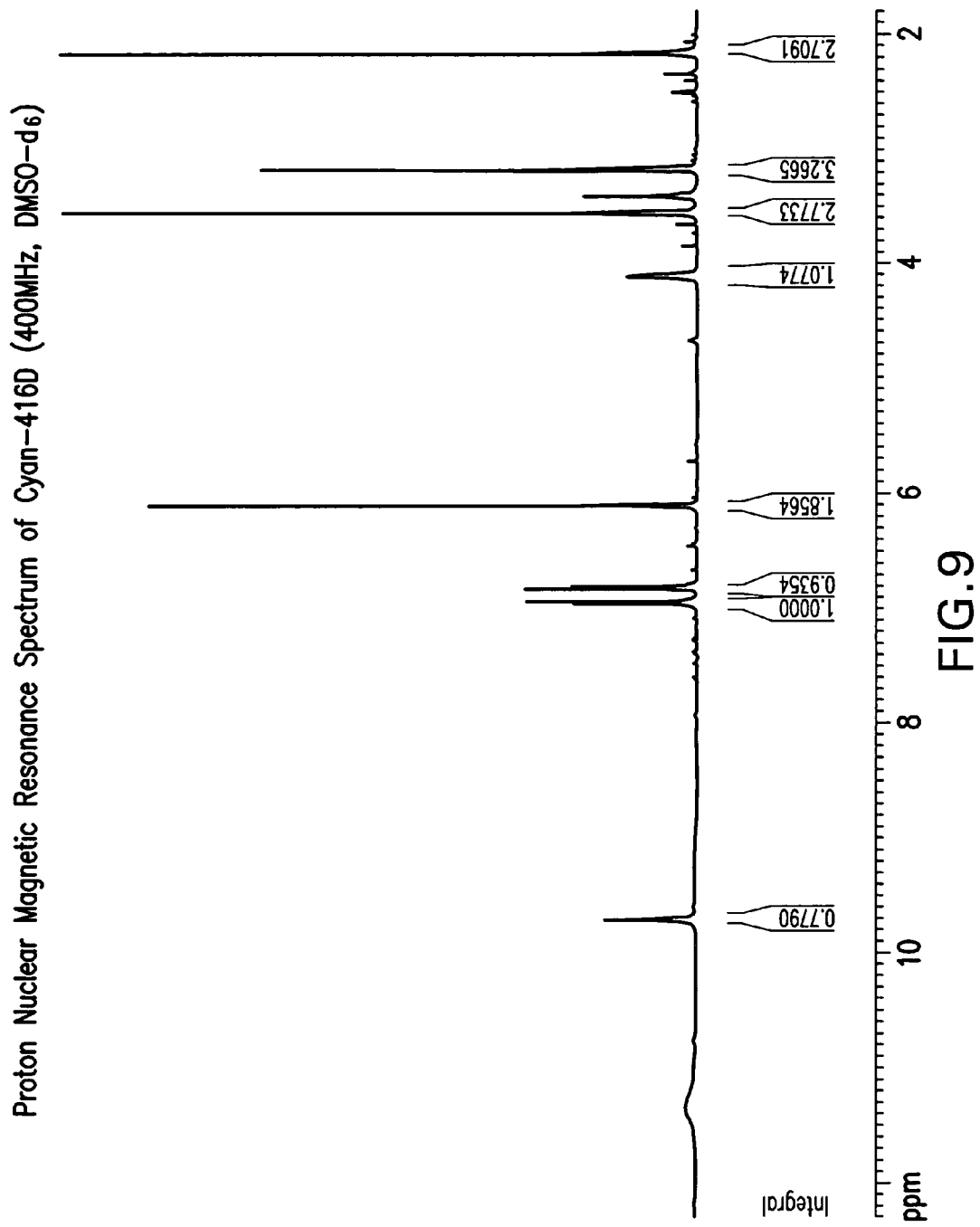
FIG. 9. shows proton nuclear magnetic resonance spectrum of Cyan-416 D in DMSO-$d_6$ at 400 MHz.

The physico-chemical characteristics of Cyan-416 D are as follows:
1. Molecular weight: 318 (ESIMS);
2. Apparent molecular formula: $C_{16}H_{14}O_7$;
3. High-resolution Fourier transform ion cyclotron resonance mass spectrum (positive): m/z 319.08104 ($MH^+$, $C_{16}H_{15}O_7$ requires 319.08177);
4. Ultraviolet absorption spectrum as shown in FIG. 4;
5. Proton nuclear magnetic resonance signals as shown in FIG. 9 (400 MHz, DMSO-$d_6$);
6. Carbon-13 nuclear magnetic resonance signals as shown in FIG. 14 (100 MHz, DMSO-$d_6$), with significant signals listed below:

| | | | | | |
|---|---|---|---|---|---|
| 199.35 | 168.06 | 161.57 | 151.23 | 147.56 | 145.65 |
| 131.24 | 122.21 | 117.52 | 112.36 | 108.96 | 107.53 |
| 51.94 | 21.65 | | | | |

The structure of the new antibiotic Cyan-416 E is:

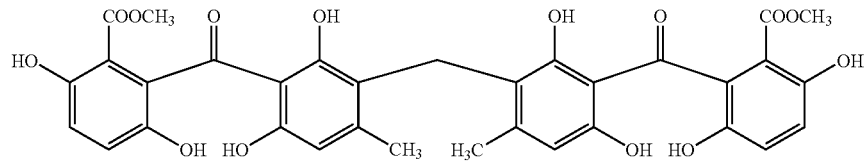

Figure 5:
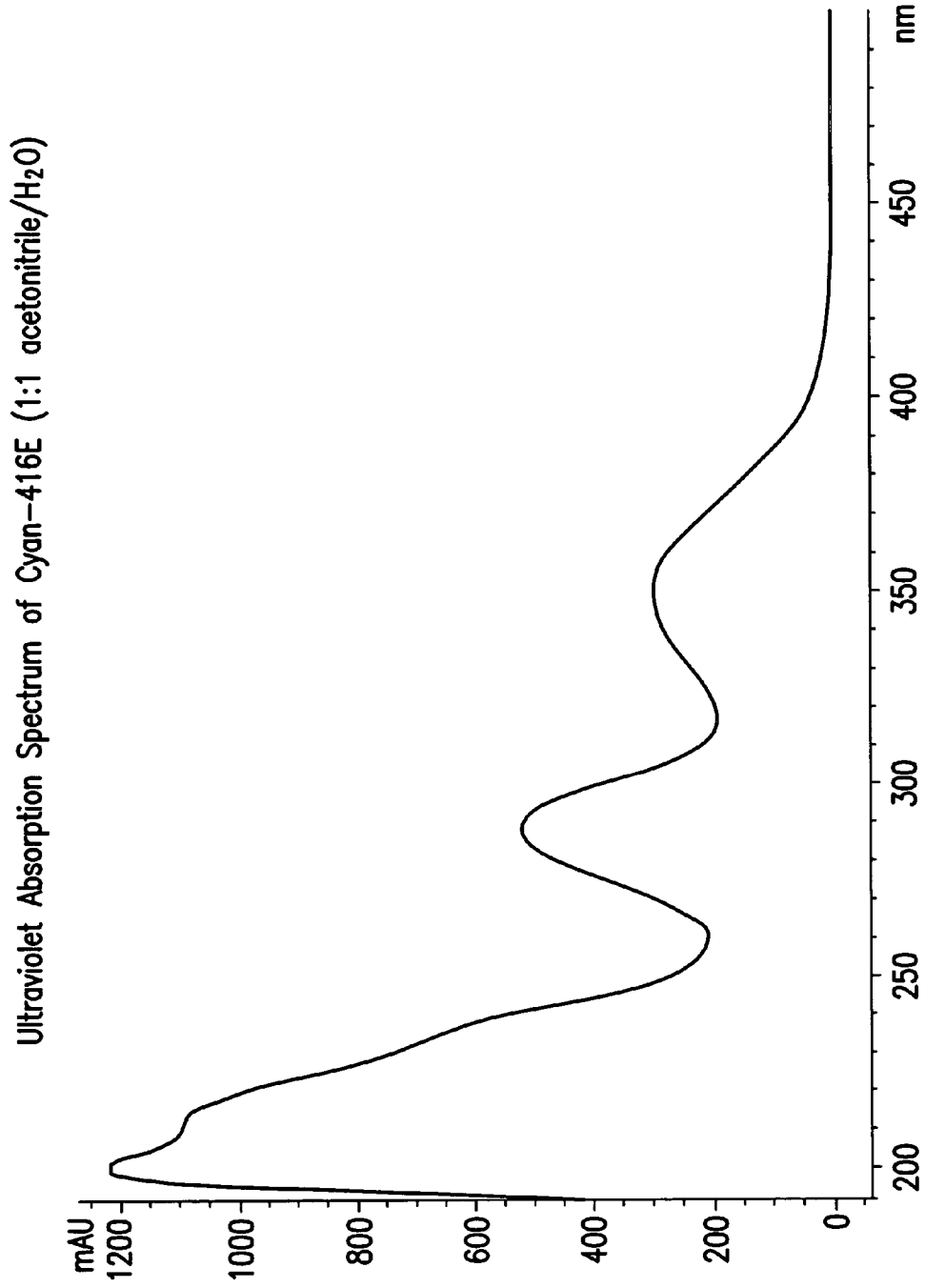
FIG. 5. shows ultraviolet absorption spectrum of Cyan-416 E.
Figure 10:
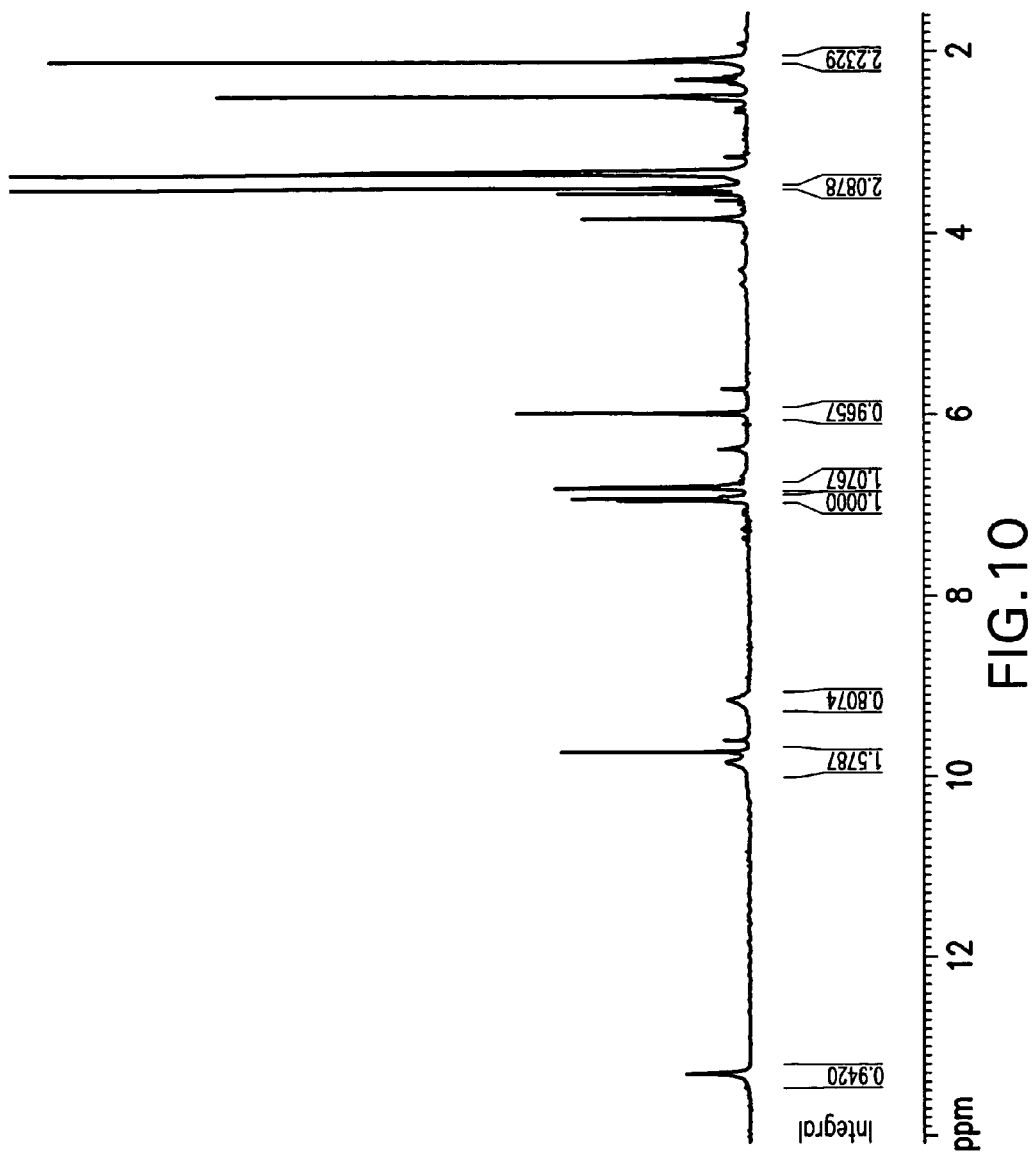
FIG. 10. shows proton nuclear magnetic resonance spectrum of Cyan-416 E in DMSO-$d_6$ at 400 MHz.

The physico-chemical characteristics of Cyan-416 E are as follows:
1. Molecular weight: 648 (ESIMS);
2. Apparent molecular formula: $C_{33}H_{28}O_{14}$;
3. High-resolution Fourier transform ion cyclotron resonance mass spectrum (negative): m/z 647.14154 (M−H, $C_{33}H_{27}O_{14}$ requires 647.14016);
4. Ultraviolet absorption spectrum as shown in FIG. 5;
5. Proton nuclear magnetic resonance signals as shown in FIG. 10 (400 MHz, DMSO-$d_6$);
6. Carbon-13 nuclear magnetic resonance signals as shown in FIG. 15 (100 MHz, DMSO-$d_6$), with significant signals listed below:

| | | | | | |
|---|---|---|---|---|---|
| 199.56 | 168.06 | 160.99 | 157.67 | 151.28 | 146.97 |
| 145.48 | 131.44 | 122.23 | 117.24 | 116.67 | 111.98 |
| 108.50 | 108.08 | 51.76 | 21.44 | 20.16 | |

A further preferred embodiment within the scope of this invention relates to the novel esters of Cyan-416 B and the process for the production of these compounds (Formula I):

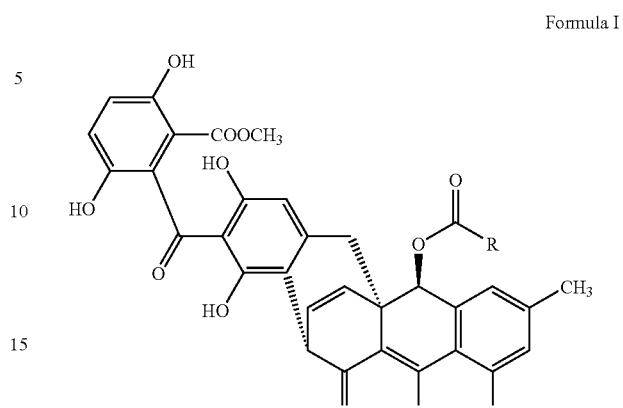

Formula I where R is straight or branched alkyl of 1 to 10 carbon atoms, alkenyl of 2 to 10 carbon atoms, cycloalkyl of 3 to 10 carbon atoms and cycloalkenyl of 3 to 10 carbon atoms.

Preferably R is —$CH_2CH_2CH_3$, —$CH(CH_3)_2$, —$CH_2CH_2CH_2CH_3$, or —$CH_2CH_2CH_2CH_2CH_3$.

The new antibacterial agents Cyan-416 A, Cyan-416 B, Cyan-416 C, Cyan-416 D and Cyan-416 E are formed during the cultivation under controlled conditions of a fungus, LL-Cyan-416, which is a strain of *Acremonium* sp. NRRL 30631.

This microorganism is maintained in the cultural collection of Wyeth Research, Pearl River, New York 10965, as culture LL-Cyan-416.

Description of LL-Cyan-416

Culture LL-Cyan-426 is that of a fungus, *Acremonium* sp., isolated from a sample collected from a mixed Douglas Fir-Hardwood forest, Crane Island Preserve, San Juan County, Washington State, in 1993. The culture has been deposited with Agricultural Research Services Culture Collection (NRRL), National Center for Agricultural Utilization Research, Agricultural Research Service, U.S. Department of Agriculture at 1815 North University Street, Peoria, Ill. 61604 as NNRL 30631.

The culture LL-Cyan-416, identified as *Acremonium* sp., exhibits the following morphological features:

On oatmeal agar (Difco Laboratories), colony attaining a diameter of 37 mm after 21 days at 25° C. Colony mat white to Yellowish White (4A2), floccose; reverse Ivory (4B3); very light brown pigment present and exudate absent.

On potato-dextrose agar (Difco) colony attaining a diameter of 39.5 mm after 21 days at 25° C. Colony mat white, sulcate; reverse Pompeian Yellow (5C6) to Golden Brown (5D7), to margin Champagne (4B4); pigment and exudate absent.

On corn meal agar (Difco) colony attaining a diameter of 24.7 mm after 21 days at 25° C. Colony mat Yellowish White (3A2), floccose; reverse Yellowish White (3A2); pigment and exudate absent.

On YpSs agar (0.4% yeast extract, 1% soluble starch, 1.5% agar (all Difco), 0.05% $K_2HPO_4$(Sigma), pH 7.2) colony attaining 39 mm after 21 days at 25° C. Colony mat white, sulcate; reverse Light Yellow (4A4) to margin Yellowish White (3A2) to Pale Yellow (3A3); pigment and exudate absent.

The characteristics of colony described were based on Methuen Handbook of colour (Kornerup, A. and Wanscher, J. H. $3^{rd}$ ed., 252 p., Eyre Methuen, London. 1978.

Mycelium micronematous; conidophores simple to sometimes branched, phialides usually arising from aerial hyphae, erect, collarette not visible, 15.5–30 um height, widest portion 1.5 um and gradually taper to 0.5 um; conidia in slim heads, asymmetrical, elongate ellipsoidal to fusoid, 3–6×1.5 um, hyaline, smooth walled; chlamydospores absent.

For the production of the new antibiotics, of the present invention are not limited to this particular organism or to organisms fully answering the above characteristics, which are given for illustration purpose only. It is desired and intended to include the use of mutants produced from this organism by various means such as exposures to X-radiation, ultraviolet radiation, N'methyl-N'-nitro-N-nitrosoguanidine, phages, and like.

ACYLATION METHOD FOR THE PREPARATION OF COMPOUNDS OF FORMULA I

The selective acylation of Cyan-416 B 1 with an anhydride of the formula (R—C(O)—)$_2$O where R is straight and branched alkyl of 1 to 10 carbon atoms, alkenyl of 2 to 10 carbon atoms, cycloalkyl of 3 to 10 carbon atoms and cycloalkenyl of 3 to 10 carbon atoms in the presence of boron trifluoride diethyl etherate ($BF_3$-$Et_2O$) affords an ester derivative of Cyan-416 B 2 as shown in Scheme 1.

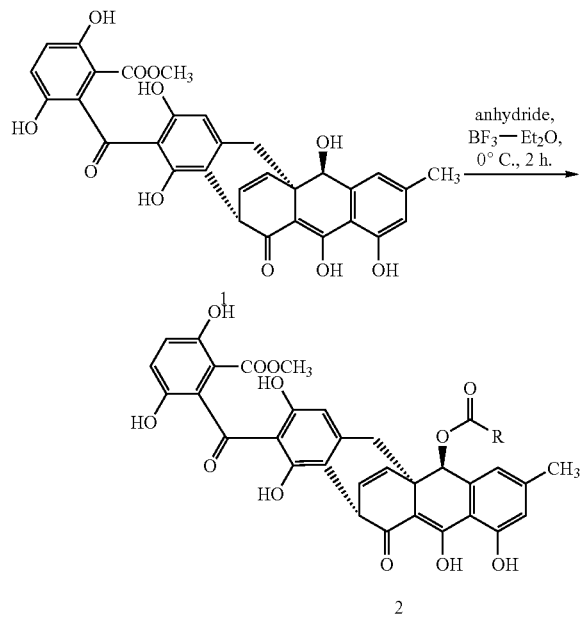

where R is straight or branched alkyl of 1 to 10 carbon atoms, alkenyl of 2 to 10 carbon atoms, cycloalkyl of 3 to 10 carbon atoms and cycloalkenyl of 3 to 10 carbon atoms.

Preferably, R is —$CH_2$ $CH_2CH_3$, —$CH(CH_3)_2$, —$CH_2CH_2CH_2CH_3$, or —$CH_2CH_2CH_2CH_2CH_3$. As further shown in Scheme 2, hydrolysis with acid of Cyan-416 A 3 affords Cyan-416 B 1.

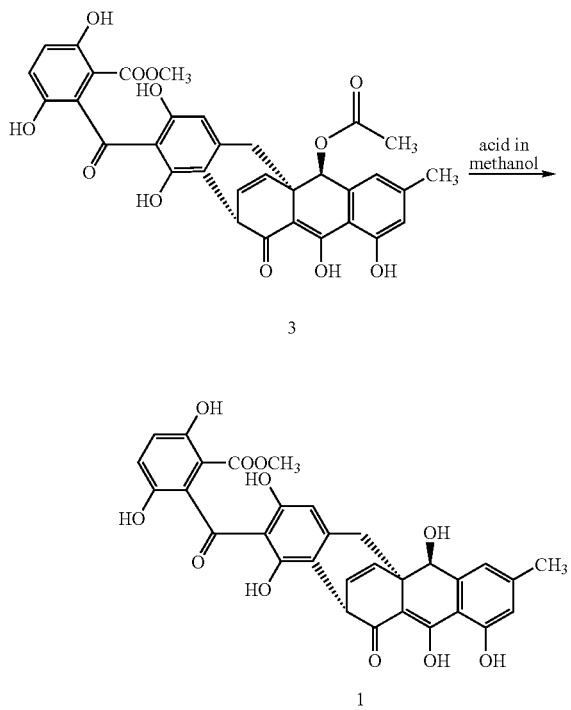

Biological Activity

Standard Pharmacological Test Procedures

The minimum inhibitory concentration (MIC), the lowest concentration of the antibiotic which inhibits growth of the test organism, is determined by the broth dilution method using Muller-Hinton II agar (Baltimore Biological Laboratories) following the recommendations of the National Committee for Clinical Laboratory Standards [Methods for dilution antimicrobial susceptibility tests for bacteria that grow aerobically. Approved standard M7-A2. National Committee for Clinical Laboratory Standards, Villanova, Pa].

An inoculum level of 5×10$^5$ CFU/ml, and a range of antibiotic concentrations (64–0.06 μ/ml) is used. The MIC is determined after the microtiter plates are incubated for 18 hours at 35° C. in an ambient air incubator. The test organisms comprise a spectrum of the Gram-positive bacteria *Staphylococcus aureus, Streptococcus pneumoniae,* and *Enterococcus* sp., the Gram-negative bacteria *Escherichia coli,* and the yeast *Candida albicans.* These organisms include recent clinical isolates that are resistant to methicillin and vancomycin. MIC data of Cyan-416 A–E are listed in Table 1 and MIC data of ester derivatives of Cyan-416 B (Formula I) are listed in Table 2.

TABLE 1

Antimicrobial Activity of Cyan-416 A, Cyan-416 B, Cyan-416 C, Cyan-416 D, and Cyan-416 E.

| | MIC (µg/ml) | | | | |
|---|---|---|---|---|---|
| Test organism | Cyan 416 A Example 3a | Cyan 416 B Example 3b | Cyan 416 C Example 3c | Cyan 416 D Example 4a | Cyan 416 E Example 4b |
| Staphylococcus aureus GC 4536 | 8 | 32 | 32 | 64 | 64 |
| Staphylococcus aureus GC 1131 | 8 | 32 | 32 | 64 | 64 |
| Staphylococcus aureus GC 2216 | 8 | 32 | 32 | 64 | 64 |
| Enterococcus faecalis GC 842 | 16 | 64 | 32 | 64 | 64 |
| Enterococcus faecalis GC 2242 | 16 | 32 | 32 | 32 | 64 |
| Enterococcus faecalis GC 4555 | 16 | 64 | 64 | 64 | 64 |
| Pseudomonas aeruginosa GC 2214 | >64 | >64 | >64 | >64 | 64 |
| Escherichia coli GC 2203 | >64 | >64 | >64 | >64 | >64 |
| Escherichia coli GC 4560 (imp) | 32 | 64 | >64 | 64 | 64 |
| Candida albicans GC 3066 | >64 | >64 | >64 | >64 | 64 |

TABLE 2

Antimicrobial Activity of Esters of Cyan-416 B (Formula I).

| | MIC (µg/ml) | | | | |
|---|---|---|---|---|---|
| Test organism | Formula I, R = $CH_3$ (Cyan416-A) Example 3a | $(CH_2)_2CH_3$ Example 6 | $CH(CH_3)_2$ Example 7 | $(CH_2)_3CH_3$ Example 8 | $(CH_2)_4CH_3$ Example 9 |
| Staphylococcus aureus GC 1131 | 8 | 8 | 4 | 4 | 4 |
| Staphylococcus aureus GC 4541 | 16 | 8 | 2 | 4 | 4 |
| Staphylococcus aureus GC 4543 | 8 | 8 | 4 | 4 | 4 |
| Staphylococcus aureus GC 2216 | 8 | 8 | 4 | 4 | 4 |
| Staphylococcus haemolyticus GC 4547 | 16 | 16 | 4 | 4 | 4 |
| Enterococcus faecalis GC 6189 | 16 | 16 | 4 | 4 | 4 |
| Enterococcus faecalis GC 4555 | 16 | 16 | 4 | 4 | 4 |
| Enterococcus faecalis GC 2242 | 16 | 8 | 4 | 4 | 4 |
| Enterococcus faecium GC 4556 | 16 | 8 | 4 | 4 | 4 |
| Enterococcus faecium GC 2243 | 8 | 16 | 8 | 4 | 4 |
| Enterococcus faecium 4558 | 8 | 8 | 2 | 2 | 2 |
| Streptococcus pneumoniae GC 1894 | 8 | 16 | 8 | 8 | 8 |
| Streptococcus pneumoniae GC 6242 | 8 | 32 | 16 | 8 | 8 |
| Escherichia coli coli GC 2203 | >128 | >128 | >128 | >128 | >128 |
| Escherichia coli GC 4560 (imp) | 32 | 16 | 8 | 8 | 8 |
| Candida albicans GC 3066 | >128 | >128 | >128 | >128 | >128 |

The in vitro antimicrobial results show that the products according to the invention have significant activity against Gram-positive bacteria tested.

Antibiotic Cyan-416 A, Cyan-416 B, Cyan-416 C, Cyan-416 D, Cyan-416 E and esters of Cyan-416 B derive their utility from antibacterial activity. For example, Cyan-416 A, Cyan-416 B, Cyan-416 C, Cyan-416 D, and Cyan-416 E may be used in the suppression of bacterial infections, as topical antibacterial agents or as a general disinfectant. Cyan-416 A, Cyan-416 B, Cyan-416 C, Cyan-416 D, and Cyan-416 E and esters of Cyan-416 B are not limited to the uses listed. In therapeutic use, the compound of this invention may be administered in the form of conventional pharmaceutical compositions appropriate for the intended use. Such compositions may be formulated as to be suitable for oral, parenteral or topical administration. The active ingredient may be combined in admixture with a nontoxic pharmaceutical carrier that may take a variety of forms depending on the form of preparation desired for administration, i.e. oral, parenteral, or topical.

When the compounds of the invention are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, from about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight. An effective amount of compound from 0.01 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition of the host undergoing therapy.

Additionally, the antibacterially effective amount of the antibiotic of the invention may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the antibiotic of the invention.

The active compound of the invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA. The active compound may also be administered parenterally or intraperitoneally. Solutions or suspensions of the active compound as a free base or pharmacologically acceptable salt can be prepared in glycerol, liquid, polyethylene glycols and mixtures thereof in oils. Under ordinary conditions of storage and use, these preparations contain a preservative. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention accordingly provides a pharmaceutical composition, which comprises a compound of this invention in combination or association with a pharmaceutically acceptable carrier. In particular, the present invention provides a pharmaceutical composition, which comprises an antibacterially effective amount of a compound of this invention and a pharmaceutically acceptable carrier.

The present invention further provides a method of treating bacterial infections in warm-blooded animals including man, which comprises administering to the afflicted warm-blooded animals an antibacterially effective amount of a compound or a pharmaceutical composition of a compound of the invention. The invention will be more fully described in conjunction with the following specific examples, which are not to be construed as limiting the scope of the invention.

As used herein an effective amount refers to the quantity of a compound of the invention which is sufficient to yield a desired therapeutic response without undue adverse side effects (such as toxicity) commensurate with a reasonable benefit/risk ratio when used in the method of this invention.

The Cyan-416 A, Cyan-416 B, Cyan-416 C, Cyan-416 D, Cyan-416 E and esters of Cyan-416 B according to the invention, have good antimicrobial activity may be used in antimicrobial compositions, especially as an antiseptic by local and general application, and as a disinfectant.

As antiseptics for human or veterinary use, the concentration of active product can vary from about 0.01% to 5% by weight according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing Cyan-416 A, Cyan-416 B, Cyan-416 C, Cyan-416 D, Cyan-416 E and esters of Cyan-416 B according to the invention are obtained using amphoteric, anionic, cationic or non-ionic surfactants at a concentration of about 0.3 to 30%, humectants such as glycols or polyethylene glycols, at a concentration of 0 to 20% ethylene oxide and polypropylene copolymers at a concentration of 0 to 20%, and an alcohol (ethanol, isopropanol, benzyl alcohol) or a polyol, such as glycerol, at a concentration of 0 to 15%, as well as agents for complexing Ca++, Mg++ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra monoethanolamide or diethanolamide, fragrances, preservatives and colorants.

It is possible to use microemulsions, micellar solutions or any other phase of the ternary or quaternary diagram of water/active principle/surfactant/co-surfactant which permits solubilization of Cyan-416 A, Cyan-416 B, Cyan-416 C, Cyan-416 D, Cyan-416 E and esters of Cyan-416 B in water. These solutions can be used in diluted or undiluted form and can be dispensed for example by means of a vasopump or liquefied or non-liquefied propellants.

With the same constituents at appropriate concentrations, the product according to the invention can also be used to prepare simple aqueous solutions or aqueous solutions in the form of sprays for making operative fields antiseptic, for postoperative treatments, for the treatment of burns, superinfected eczema, gluteal erythema, wounds or acne, or for deodorants.

Simple alcoholic solutions or alcoholic solutions in the form of sprays containing 20 to 80% by weight of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefosse). These solutions are to be used for making the skin antiseptic before puncture, for preparing the operative field, by nursing staff for making their hands antiseptic and for treating closed infected dermatosis, folliculitis, perionychia or acne. Cyan-416 A, Cyan-416 B, Cyan-416 C, Cyan-416 D, Cyan-416 E and esters of Cyan-416 B according to the invention can be applied in the form of creams together with the fatty substances normally found in the preparation of creams or emulsions. Cyan-416 A, Cyan-416 B, Cyan-416 C, Cyan-416 D, Cyan-416 E and Cyan-416 B and esters of Cyan-416 B according to the invention can also be used in animals for indications such as the prevention or treatment of infected lesions. In this case, the pharmaceutical compositions are similar to those used in man, in particular creams sprays or solutions.

Moreover, the rapid lethal action on germs of Cyan-416 A, Cyan-416 B, Cyan-416 C, Cyan-416 D, Cyan-416 E and esters of Cyan-416 B according to the invention may be used as surface disinfectants at concentrations which can vary from about 0.1 to 4% by weight. In this case, Cyan-416 A, Cyan-416 B, Cyan-416 C, Cyan-416 D, Cyan-416 E and esters of Cyan-416 B is used in preparations such as aqueous or non-aqueous foaming detergent solutions, sprays or nebulizers. This type of preparation is particularly useful in the hospital or veterinary sectors. These preparations can contain the same constituents as those used in the antiseptic formulations, although a variety of organic solvents may be added.

General Fermentation Conditions

Culture LL-Cyan-416 Acremonium sp. NRRL30631 is inoculated on moist milk-filter paper placed on the surface of a solid, agar medium containing agar, malt extract, peptone, and yeast extract and incubated under stationary conditions at 22° C.

General Isolation Procedures of Antibiotics Cyan-416 A, B, C, D, and E

The Cyan-416 A, Cyan-416 B, Cyan-416 C, Cyan-416 D, and Cyan-416 E are recovered from the fermentation broth by extracting cells with methanol. The methanol extract is evaporated under reduced pressure and the concentrate purified by HPLC on C18 columns using acidic acetonitrile in water to afford Cyan-416 A, Cyan-416 B, Cyan-416 C, Cyan-416 D, and Cyan-416 E.

The invention is further described in conjunction with the following non-limited examples.

EXAMPLE 1

Inoculum Preparation

Fungal culture LL-Cyan-416 is plated on Bennett's agar medium (10 g/l Sigma D-glucose, 1 g/l Difco beef extract, 1 g/l Difco yeast extract, 2 g/l N–Z amine A, 20 g/l Difco agar) from a frozen 25% glycerol stock culture and then incubated at 22° C. A small agar slice bearing mycelial growth is used to inoculate 50 ml of Difco potato-dextrose broth in a 250-ml Erlenmeyer flask. This liquid seed culture is shaken at 200 rpm at 22° C. for one week, and then used to inoculate production medium.

EXAMPLE 2

Fermentation

Production medium (1 L) consisted of malt extract agar (25 g Difco malt extract, 5 g Difco peptone, 0.5 g Difco yeast extract, 20 g Difco agar) that has been sterilized and poured into a 30×20×13 cm polypropylene tray covered with aluminum foil. The solidified agar is then overlaid with a sterile 28×46 cm sheet of nongauze milk-filter paper cut from 18×22 in strips (KenAG Animal Care Group, Ashland, Ohio) that had been sterilized separately. The production medium is inoculated by pipeting 50 ml of seed culture fluid onto the sheet of milk-filter paper. The inoculated tray culture is incubated stationary at 22° C. After 2 weeks of incubation, the milk-filter paper bearing prolific mycelial growth is peeled from the surface of the agar, lyophilized for 5 days, and then extracted with methanol (1.2 L).

EXAMPLES 3a, 3b, and 3c

Purification of New Antibiotics Cyan-416 A(3a), Cyan-416 B(3b), and Cyan-416 C(3c)

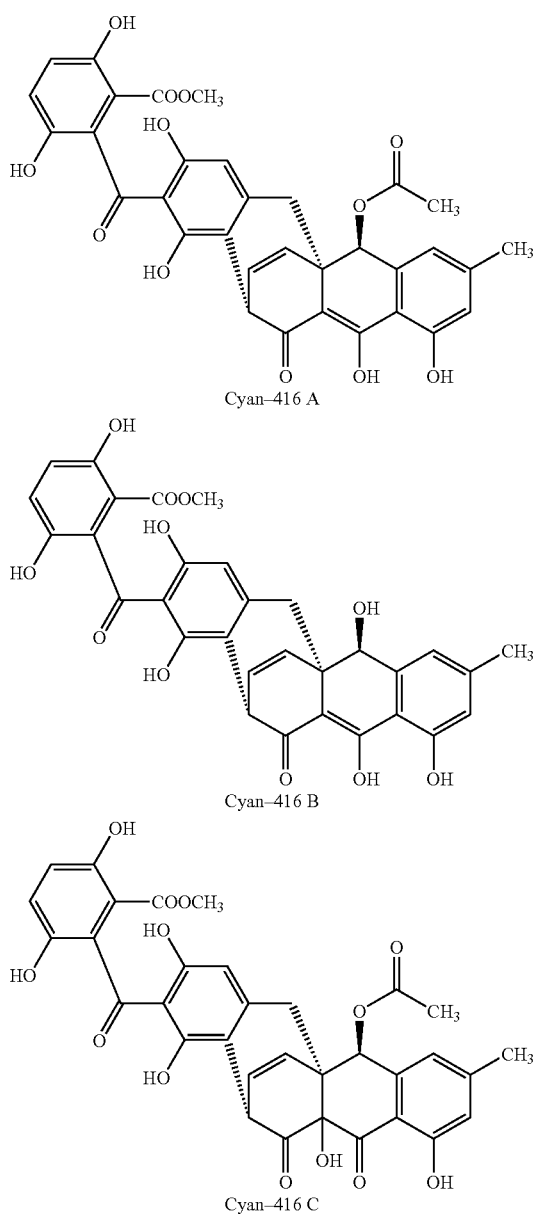

The methanol extract obtained in EXAMPLE 2 is chromatographed by reverse phase HPLC on a C18 column (YMC ODS-A, 10 µm particle size, 70×500 mm), using a linear gradient of 30–100% acetonitrile in water containing 0.01% trifluoroacetic acid (TFA) over 35 min. Four fractions at 27.5, 30.5, 35.0, and 38.37 minutes are collected. The materials from the later three fractions at 30.5, 35.0, and 38.37 minutes are respectively purified by a different HPLC system (YMC ODS-A, 5 µm, 30×250 mm column, 40–75% acetonitrile in water containing 0.01% TFA over 30 min) to afford cyan-416 B (4.5 mg), cyan-416 C (4.2 mg), and cyan-416 A (130.8 mg), all as yellow amorphous powders.

EXAMPLES 4a and 4b

Purification of New Antibiotics Cyan-416 D(4a) and Cyan-416 E(4b)

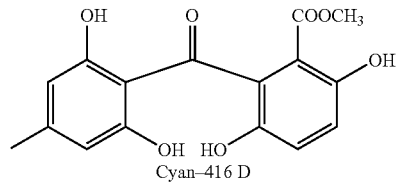
Cyan–416 D

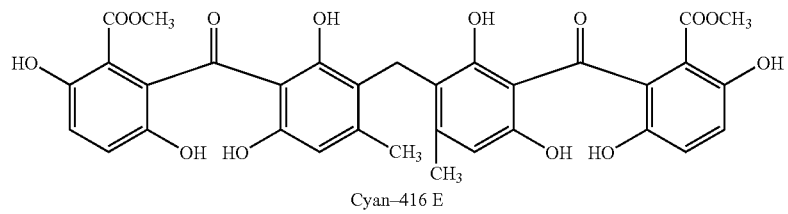
Cyan–416 E

The material from the first fraction at 27.5 minutes described in EXAMPLE 3 is further separated by HPLC (YMC ODS-A, 5 μm, 30×250 mm column, 30–100% acetonitrile in water containing 0.01% TFA over 30 min) to afford pure Cyan-416 D (21.0 mg) and cyan-416 E (3.1 mg), both as pale yellow amorphous powders.

EXAMPLE 5

Production of Cyan-416 B from Cyan-416 A

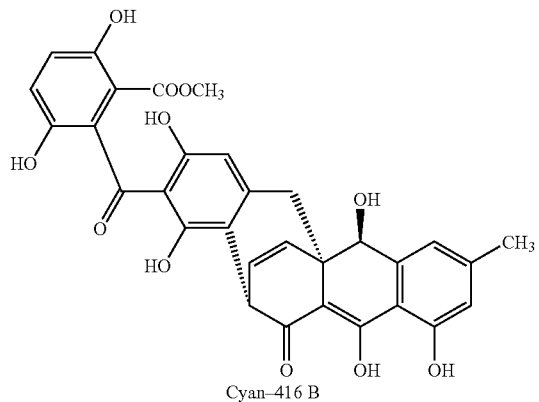
Cyan–416 B

A solution of Cyan-416 A (120.0 mg) in 1 ml 1:1 $Et_2O/MeOH$ containing 0.5 M hydrochloric acid is stirred at ambient temperature for 24 hours. The purification of the resulting mixture by HPLC (same system as in Example 4) affords Cyan-416 B (102.5 mg). ESIMS (negative) m/z 571 $(M-H)^-$.

EXAMPLE 6

Cyan-416 B Butyrate

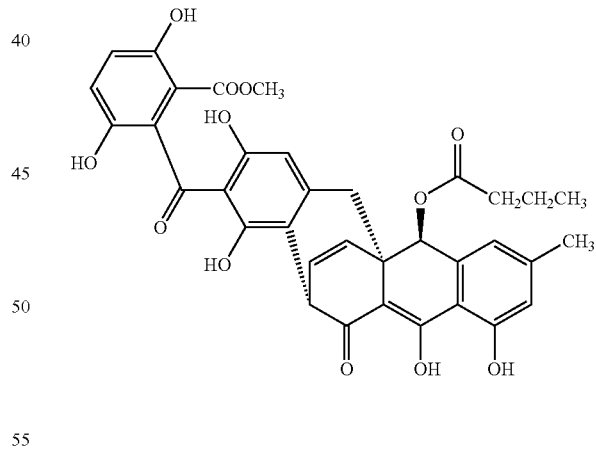

To a solution of Cyan-416 B (20.0 mg) in dry tetrahydrofuran (0.5 ml), is added dropwise a solution of 7% (v/v) of $BF_3$-$Et_2O$ in butyric anhydride (0.2 ml) at 0° C. The reaction mixture is stirred at this temperature for 2 hours before methanol (2.0 ml) is added. The resulting solution is stirred for 0.5 hour at ambient temperature and then chromatographed by HPLC on a C18 column (YMC ODS-A, 5 μm particle size, 30×250 mm) using a linear gradient (40–100% acetonitrile. in water containing 0.01% TFA in 30 minutes) to afford Cyan-416 B butyrate (15.3 mg, Formula I, R=$CH_2CH_2CH_3$). ESIMS (negative) m/z 641 $(M-H)^-$.

EXAMPLE 7

Cyan-416 B Isobutyrate

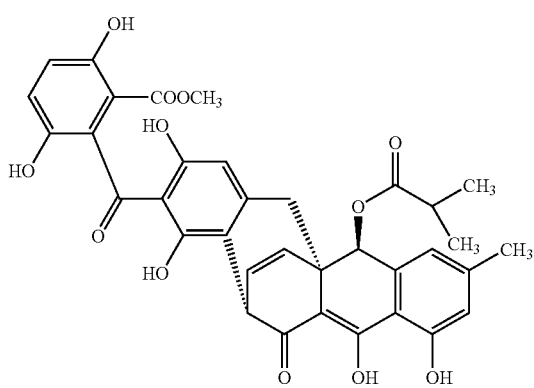

Cyan-416 B (20.0 mg) is acylated using isobutyric anhydride to replace butyric anhydride in the procedure described in EXAMPLE 6 to afford Cyan-416 B isobutyrate (12.0 mg, Formula I, R=CH(CH$_3$)$_2$). ESIMS (negative) m/z 641 (M−H)$^-$.

EXAMPLE 8

Cyan-416 B Pentanoate

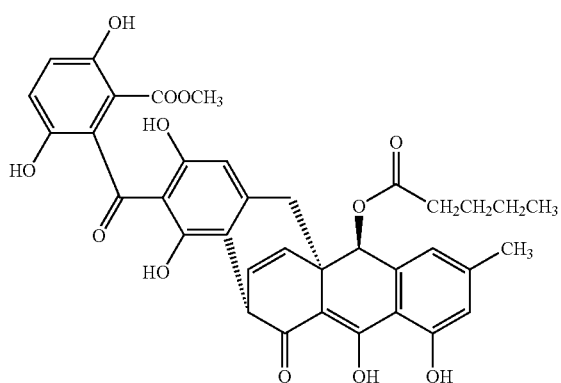

Cyan-416 B (20.0 mg) is acylated using pentanoic anhydride to replace butyric anhydride in the procedure described in EXAMPLE 6 to afford Cyan-416 B pentanoate (17.2 mg, Formula I, R=CH$_2$CH$_2$CH$_2$CH$_3$). ESIMS (negative) m/z 655 (M−H)$^-$.

EXAMPLE 9

Cyan-416 B Hexanoate

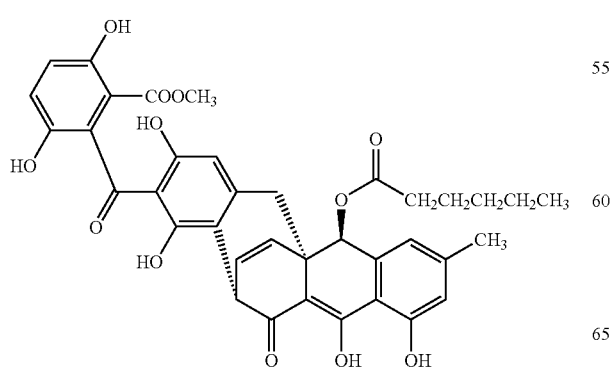

Cyan-416 B (20.0 mg) is acylated using hexanoic anhydride to replace butyric anhydride in the procedure described in EXAMPLE 6 to afford Cyan-416 B hexanoate (17.8 mg, Formula I, R=CH$_2$CH$_2$CH$_2$CH$_2$CH$_3$). ESIMS (negative) m/z 669 (M−H)$^-$.

What is claimed is:

1. The compound which has the structure

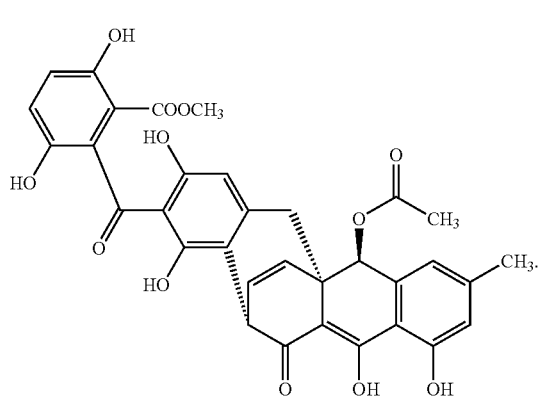

2. The compound which has the structure

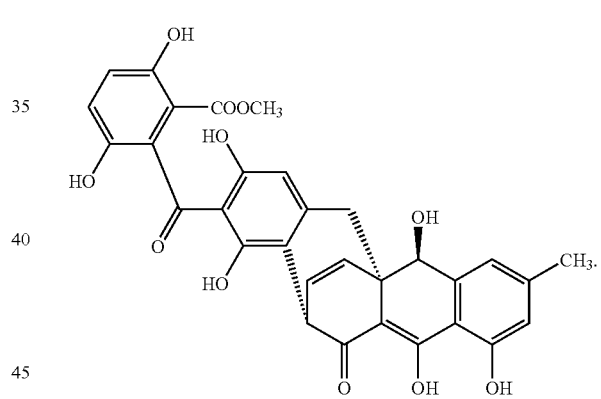

3. The compound which has the structure

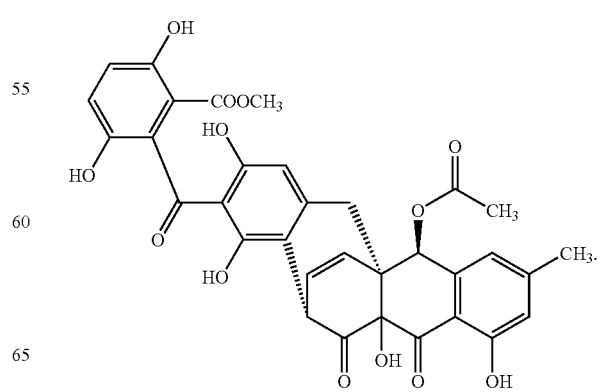

4. The compound which has the structure:

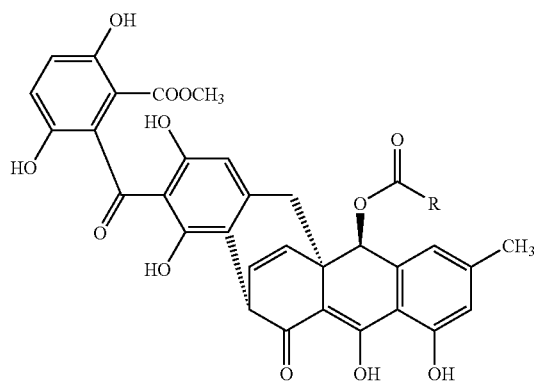

wherein R is straight or branched alkyl of 1 to 10 carbon atoms, alkenyl of 2 to 10 carbon atoms, cycloalkyl of 3 to 10 carbon atoms and cycloalkenyl of 3 to 10 carbon atoms.

5. The compound according to claim 4 where R is —$CH_2CH_2CH_3$, —$CH(CH_3)_2$, —$CH_2CH_2CH_2CH_3$, or —$CH_2CH_2CH_2CH_2CH_3$.

6. A pharmaceutical composition comprising an effective amount of a compound of claim 1 together with a pharmaceutically acceptable carrier.

7. A pharmaceutical composition comprising an effective amount of a compound of claim 2 together with a pharmaceutically acceptable carrier.

8. A pharmaceutical composition comprising an effective amount of a compound of claim 3 together with a pharmaceutically acceptable carrier.

9. A pharmaceutical composition comprising an effective amount of a compound of claim 4 together with a pharmaceutically acceptable carrier.

10. A pharmaceutical or disinfectant composition which contains an effective antimicrobial, antiseptic or disinfectant amount of the compound of claim 1 as an active ingredient.

11. A pharmaceutical or disinfectant composition which contains an effective antimicrobial, antiseptic or disinfectant amount of a compound of claim 2 as an active ingredient.

12. A pharmaceutical or disinfectant composition which contains an effective antimicrobial, antiseptic or disinfectant amount of a compound of claim 3 as an active ingredient.

13. A pharmaceutical or disinfectant composition which contains an effective antimicrobial, antiseptic or disinfectant amount of a compound of claim 4 as an active ingredient.

* * * * *